(12) United States Patent  (10) Patent No.: US 8,226,891 B2
Sloan et al.  (45) Date of Patent: Jul. 24, 2012

(54) ANALYTE MONITORING DEVICES AND METHODS THEREFOR

(75) Inventors: Mark K. Sloan, Redwood City, CA (US); R. Curtis Jennewine, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1141 days.

(21) Appl. No.: 11/396,182

(22) Filed: Mar. 31, 2006

(65) Prior Publication Data

US 2009/0105570 A1   Apr. 23, 2009

(51) Int. Cl.
*G01N 33/50* (2006.01)
*A61B 5/00* (2006.01)
*A61B 5/157* (2006.01)

(52) U.S. Cl. ....... 422/82.02; 604/504; 435/14; 435/970; 705/3

(58) Field of Classification Search .............. 604/504; 422/430, 82.01, 82.02; 705/3; 435/14, 970
See application file for complete search history.

(56) References Cited

U.S. PATENT DOCUMENTS

| | | |
|---|---|---|
| 2,755,036 A | 7/1956 | Mikko |
| 3,260,656 A | 7/1966 | Ross, Jr. |
| 3,304,413 A | 2/1967 | Lehmann et al. |
| 3,581,062 A | 5/1971 | Aston |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,776,832 A | 12/1973 | Oswin et al. |
| 3,837,339 A | 9/1974 | Aisenberg et al. |
| 3,919,051 A | 11/1975 | Koch et al. |
| 3,923,060 A | 12/1975 | Ellinwood, Jr. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,003,379 A | 1/1977 | Ellinwood, Jr. |
| 4,008,717 A | 2/1977 | Kowarski |
| 4,016,866 A | 4/1977 | Lawton |
| 4,021,718 A | 5/1977 | Konrad |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |

(Continued)

FOREIGN PATENT DOCUMENTS

DE   2903216   8/1979
(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

(Continued)

*Primary Examiner* — In Suk Bullock
*Assistant Examiner* — Paul Hyun
(74) *Attorney, Agent, or Firm* — Jackson & Co., LLP

(57) ABSTRACT

Method and apparatus for performing a discrete glucose testing and bolus dosage determination including a glucose meter with bolus calculation function are provided.

26 Claims, 5 Drawing Sheets

U.S. PATENT DOCUMENTS

| | | | |
|---|---|---|---|
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danninger et al. |
| 4,172,770 A | 10/1979 | Semersky et al. |
| 4,178,916 A | 12/1979 | McNamara |
| 4,193,026 A | 3/1980 | Finger et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,467,811 A | 8/1984 | Clark, Jr. |
| 4,469,110 A | 9/1984 | Slama |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,601,707 A | 7/1986 | Albisser et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,903 A | 8/1987 | Cable et al. |
| 4,686,624 A | 8/1987 | Blum et al. |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhart |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |
| 4,844,076 A | 7/1989 | Lesho et al. |
| 4,845,035 A | 7/1989 | Fanta et al. |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |

| Patent | Date | Inventor |
|---|---|---|
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuki et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,236,143 A | 8/1993 | Dragon |
| 5,237,993 A | 8/1993 | Skrabal |
| 5,246,867 A | 9/1993 | Lakowicz et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,449 A | 7/1994 | Cunningham |
| 5,333,615 A | 8/1994 | Craelius et al. |
| 5,337,258 A | 8/1994 | Dennis |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,348 A | 10/1994 | Bellio et al. |
| 5,356,786 A | 10/1994 | Heller et al. |
| 5,358,135 A | 10/1994 | Robbins et al. |
| 5,358,514 A | 10/1994 | Schulman et al. |
| 5,360,404 A | 11/1994 | Novacek et al. |

| | | | | | |
|---|---|---|---|---|---|
| 5,364,797 A | 11/1994 | Olson et al. | 5,549,113 A | 8/1996 | Halleck et al. |
| 5,366,609 A | 11/1994 | White et al. | 5,549,115 A | 8/1996 | Morgan et al. |
| 5,368,028 A | 11/1994 | Palti | 5,552,027 A | 9/1996 | Birkle et al. |
| 5,370,622 A | 12/1994 | Livingston et al. | 5,554,166 A | 9/1996 | Lange et al. |
| 5,371,687 A | 12/1994 | Holmes, II et al. | 5,556,524 A | 9/1996 | Albers |
| 5,371,734 A | 12/1994 | Fischer | 5,560,357 A | 10/1996 | Faupel et al. |
| 5,372,133 A | 12/1994 | Hogen Esch | 5,562,713 A | 10/1996 | Silvian |
| 5,372,427 A | 12/1994 | Padovani et al. | 5,565,085 A | 10/1996 | Ikeda et al. |
| 5,376,070 A | 12/1994 | Purvis et al. | 5,567,302 A | 10/1996 | Song et al. |
| 5,376,251 A | 12/1994 | Kaneko et al. | 5,568,806 A | 10/1996 | Cheney, II et al. |
| 5,377,258 A | 12/1994 | Bro | 5,569,186 A | 10/1996 | Lord et al. |
| 5,378,628 A | 1/1995 | Gratzel et al. | 5,569,212 A | 10/1996 | Brown |
| 5,379,238 A | 1/1995 | Stark | 5,573,647 A | 11/1996 | Maley et al. |
| 5,379,764 A | 1/1995 | Barnes et al. | 5,575,895 A | 11/1996 | Ikeda et al. |
| 5,380,422 A | 1/1995 | Negishi et al. | 5,580,527 A | 12/1996 | Bell et al. |
| 5,382,346 A | 1/1995 | Uenoyama et al. | 5,580,794 A | 12/1996 | Allen |
| 5,387,327 A | 2/1995 | Khan | 5,582,184 A | 12/1996 | Erickson et al. |
| 5,390,671 A | 2/1995 | Lord et al. | 5,582,697 A | 12/1996 | Ikeda et al. |
| 5,391,250 A | 2/1995 | Cheney, II et al. | 5,582,698 A | 12/1996 | Flaherty et al. |
| 5,393,903 A | 2/1995 | Gratzel et al. | 5,584,813 A | 12/1996 | Livingston et al. |
| 5,395,504 A | 3/1995 | Saurer et al. | 5,586,553 A | 12/1996 | Halili et al. |
| 5,399,823 A | 3/1995 | McCusker | 5,589,326 A | 12/1996 | Deng et al. |
| 5,400,782 A | 3/1995 | Beaubiah | 5,593,852 A | 1/1997 | Heller et al. |
| 5,408,999 A | 4/1995 | Singh et al. | 5,594,906 A | 1/1997 | Holmes, II et al. |
| 5,410,326 A | 4/1995 | Goldstein | 5,596,150 A | 1/1997 | Arndy et al. |
| 5,410,471 A | 4/1995 | Alyfuku et al. | 5,596,994 A | 1/1997 | Bro |
| 5,410,474 A | 4/1995 | Fox | 5,601,435 A | 2/1997 | Quy |
| 5,411,647 A | 5/1995 | Johnson et al. | 5,601,694 A | 2/1997 | Maley et al. |
| 5,413,690 A | 5/1995 | Kost et al. | 5,605,152 A | 2/1997 | Slate et al. |
| 5,422,246 A | 6/1995 | Koopal et al. | 5,609,575 A | 3/1997 | Larson et al. |
| 5,425,868 A | 6/1995 | Pedersen | 5,611,900 A | 3/1997 | Worden et al. |
| 5,431,160 A | 7/1995 | Wilkins | 5,615,135 A | 3/1997 | Waclawsky et al. |
| 5,431,691 A | 7/1995 | Snell et al. | 5,615,671 A | 4/1997 | Schoonen et al. |
| 5,431,921 A | 7/1995 | Thombre | 5,616,222 A | 4/1997 | Maley et al. |
| 5,433,710 A | 7/1995 | Van Antwerp et al. | 5,617,851 A | 4/1997 | Lipkovker |
| 5,437,973 A | 8/1995 | Vadgama et al. | 5,623,925 A | 4/1997 | Swenson et al. |
| 5,437,999 A | 8/1995 | Diebold et al. | 5,623,933 A | 4/1997 | Amano et al. |
| 5,438,271 A | 8/1995 | White et al. | 5,628,309 A | 5/1997 | Brown |
| 5,445,611 A | 8/1995 | Eppstein et al. | 5,628,310 A | 5/1997 | Rao et al. |
| 5,445,920 A | 8/1995 | Saito | 5,628,890 A | 5/1997 | Carter et al. |
| 5,456,692 A | 10/1995 | Smith, Jr. et al. | 5,629,981 A | 5/1997 | Nerlikar |
| 5,456,940 A | 10/1995 | Funderburk | 5,637,095 A | 6/1997 | Nason et al. |
| 5,458,140 A | 10/1995 | Eppstein et al. | 5,640,764 A | 6/1997 | Strojnik |
| 5,460,618 A | 10/1995 | Harreld | 5,640,954 A | 6/1997 | Pfeiffer et al. |
| 5,462,525 A | 10/1995 | Srisathapat et al. | 5,643,212 A | 7/1997 | Coutre et al. |
| 5,462,645 A | 10/1995 | Albery et al. | 5,647,853 A | 7/1997 | Feldmann et al. |
| 5,466,218 A | 11/1995 | Srisathapat et al. | 5,650,062 A | 7/1997 | Ikeda et al. |
| 5,467,778 A | 11/1995 | Catt et al. | 5,651,767 A | 7/1997 | Schulman et al. |
| 5,469,846 A | 11/1995 | Khan | 5,651,869 A | 7/1997 | Yoshioka et al. |
| 5,472,317 A | 12/1995 | Field et al. | 5,653,239 A | 8/1997 | Pompei et al. |
| 5,476,460 A | 12/1995 | Montalvo | 5,660,163 A | 8/1997 | Schulman et al. |
| 5,477,855 A | 12/1995 | Schindler et al. | 5,665,065 A | 9/1997 | Colman et al. |
| 5,482,473 A | 1/1996 | Lord et al. | 5,665,222 A | 9/1997 | Heller et al. |
| 5,484,404 A | 1/1996 | Schulman et al. | 5,667,983 A | 9/1997 | Abel et al. |
| 5,487,751 A | 1/1996 | Radons et al. | 5,670,031 A | 9/1997 | Hintsche et al. |
| 5,491,474 A | 2/1996 | Suni et al. | 5,678,571 A | 10/1997 | Brown |
| 5,494,562 A | 2/1996 | Maley et al. | 5,679,690 A | 10/1997 | Andre et al. |
| 5,496,453 A | 3/1996 | Uenoyama et al. | 5,680,858 A | 10/1997 | Hansen et al. |
| 5,497,772 A | 3/1996 | Schulman et al. | 5,682,233 A | 10/1997 | Brinda |
| 5,501,956 A | 3/1996 | Wada et al. | 5,686,717 A | 11/1997 | Knowles et al. |
| 5,505,709 A | 4/1996 | Funderburk | 5,695,623 A | 12/1997 | Michel et al. |
| 5,505,713 A | 4/1996 | Van Antwerp et al. | 5,695,949 A | 12/1997 | Galen et al. |
| 5,507,288 A | 4/1996 | Bocker et al. | 5,701,894 A | 12/1997 | Cherry et al. |
| 5,508,171 A | 4/1996 | Walling et al. | 5,704,922 A | 1/1998 | Brown |
| 5,509,410 A | 4/1996 | Hill et al. | 5,707,502 A | 1/1998 | McCaffrey et al. |
| 5,514,103 A | 5/1996 | Srisathapat et al. | 5,708,247 A | 1/1998 | McAleer et al. |
| 5,514,253 A | 5/1996 | Davis et al. | 5,710,630 A | 1/1998 | Essenpreis et al. |
| 5,514,718 A | 5/1996 | Lewis et al. | 5,711,001 A | 1/1998 | Bussan et al. |
| 5,518,006 A | 5/1996 | Mawhirt et al. | 5,711,297 A | 1/1998 | Iliff |
| 5,520,787 A | 5/1996 | Hanagan et al. | 5,711,861 A | 1/1998 | Ward et al. |
| 5,522,865 A | 6/1996 | Schulman et al. | 5,711,862 A | 1/1998 | Sakoda et al. |
| 5,525,511 A | 6/1996 | D'Costa | 5,711,868 A | 1/1998 | Maley et al. |
| 5,526,120 A | 6/1996 | Jina et al. | 5,718,234 A | 2/1998 | Warden et al. |
| 5,527,307 A | 6/1996 | Srisathapat et al. | 5,720,733 A | 2/1998 | Brown |
| 5,529,676 A | 6/1996 | Maley et al. | 5,720,862 A | 2/1998 | Hamamoto et al. |
| 5,531,878 A | 7/1996 | Vadgama et al. | 5,721,783 A | 2/1998 | Anderson |
| 5,538,511 A | 7/1996 | Van Antwerp et al. | 5,722,397 A | 3/1998 | Eppstein |
| 5,545,152 A | 8/1996 | Funderburk et al. | 5,727,548 A | 3/1998 | Hill et al. |
| 5,545,191 A | 8/1996 | Mann et al. | 5,730,124 A | 3/1998 | Yamauchi |

| | | | | | |
|---|---|---|---|---|---|
| 5,730,654 A | 3/1998 | Brown | 5,951,492 A | 9/1999 | Douglas et al. |
| 5,735,273 A | 4/1998 | Kurnik et al. | 5,951,521 A | 9/1999 | Mastrototaro et al. |
| 5,735,285 A | 4/1998 | Albert et al. | 5,951,836 A | 9/1999 | McAleer et al. |
| 5,741,211 A | 4/1998 | Renirie et al. | 5,954,643 A | 9/1999 | Van Antwerp |
| 5,741,688 A | 4/1998 | Oxenboll et al. | 5,954,685 A | 9/1999 | Tierney |
| 5,746,217 A | 5/1998 | Erickson et al. | 5,954,700 A | 9/1999 | Kovelman |
| 5,750,926 A | 5/1998 | Schulman et al. | 5,956,501 A | 9/1999 | Brown |
| 5,770,028 A | 6/1998 | Maley et al. | 5,957,854 A | 9/1999 | Besson et al. |
| 5,771,001 A | 6/1998 | Cobb | 5,957,890 A | 9/1999 | Mann et al. |
| 5,771,890 A | 6/1998 | Tamada | 5,957,958 A | 9/1999 | Schulman et al. |
| 5,772,586 A | 6/1998 | Heinonen et al. | 5,960,403 A | 9/1999 | Brown |
| 5,777,060 A | 7/1998 | Van Antwerp | 5,961,451 A | 10/1999 | Reber et al. |
| 5,779,665 A | 7/1998 | Mastrototaro et al. | 5,964,993 A | 10/1999 | Blubaugh, Jr. et al. |
| 5,781,024 A | 7/1998 | Blomberg et al. | 5,965,380 A | 10/1999 | Heller et al. |
| 5,782,814 A | 7/1998 | Brown et al. | 5,968,839 A | 10/1999 | Blatt et al. |
| 5,785,681 A | 7/1998 | Indravudh | 5,971,922 A | 10/1999 | Arita et al. |
| 5,786,439 A | 7/1998 | Van Antwerp et al. | 5,971,941 A | 10/1999 | Simons et al. |
| 5,786,584 A | 7/1998 | Button et al. | 5,974,124 A | 10/1999 | Schlueter, Jr. et al. |
| 5,788,678 A | 8/1998 | Van Antwerp | 5,977,476 A | 11/1999 | Guha et al. |
| 5,791,344 A | 8/1998 | Schulman et al. | 5,981,294 A | 11/1999 | Blatt et al. |
| 5,792,117 A | 8/1998 | Brown | 5,989,409 A | 11/1999 | Kurnik et al. |
| 5,793,292 A | 8/1998 | Ivey | 5,994,476 A | 11/1999 | Shin et al. |
| 5,800,420 A | 9/1998 | Gross et al. | 5,995,860 A | 11/1999 | Sun et al. |
| 5,804,048 A | 9/1998 | Wong et al. | 5,997,476 A | 12/1999 | Brown |
| 5,807,315 A | 9/1998 | Van Antwerp et al. | 5,999,848 A | 12/1999 | Gord et al. |
| 5,807,375 A | 9/1998 | Gross et al. | 5,999,849 A | 12/1999 | Gord et al. |
| 5,814,599 A | 9/1998 | Mitragotri et al. | 6,001,067 A | 12/1999 | Shults et al. |
| 5,820,551 A | 10/1998 | Hill et al. | 6,002,954 A | 12/1999 | Van Antwerp et al. |
| 5,820,570 A | 10/1998 | Erickson et al. | 6,002,961 A | 12/1999 | Mitragotri et al. |
| 5,820,622 A | 10/1998 | Gross et al. | 6,004,441 A | 12/1999 | Fujiwara et al. |
| 5,822,715 A | 10/1998 | Worthington et al. | 6,011,984 A | 1/2000 | Van Antwerp et al. |
| 5,825,488 A | 10/1998 | Kohl et al. | 6,014,577 A | 1/2000 | Henning et al. |
| 5,827,179 A | 10/1998 | Lichter et al. | 6,018,678 A | 1/2000 | Mitragotri et al. |
| 5,827,183 A | 10/1998 | Kurnik et al. | 6,023,629 A | 2/2000 | Tamada |
| 5,827,184 A | 10/1998 | Netherly et al. | 6,024,699 A | 2/2000 | Surwit et al. |
| 5,828,943 A | 10/1998 | Brown | 6,026,320 A | 2/2000 | Carlson et al. |
| 5,830,341 A | 11/1998 | Gilmartin | 6,027,459 A | 2/2000 | Shain et al. |
| 5,832,448 A | 11/1998 | Brown | 6,027,692 A | 2/2000 | Galen et al. |
| 5,834,224 A | 11/1998 | Ruger et al. | 6,032,059 A | 2/2000 | Henning et al. |
| 5,837,454 A | 11/1998 | Cozzette et al. | 6,032,199 A | 2/2000 | Lim et al. |
| 5,837,546 A | 11/1998 | Allen et al. | 6,033,866 A | 3/2000 | Guo et al. |
| 5,840,020 A | 11/1998 | Heinonen et al. | 6,035,237 A | 3/2000 | Schulman et al. |
| 5,842,983 A | 12/1998 | Abel et al. | 6,040,194 A | 3/2000 | Chick et al. |
| 5,843,140 A | 12/1998 | Strojnik | 6,041,253 A | 3/2000 | Kost et al. |
| 5,846,702 A | 12/1998 | Deng et al. | 6,043,437 A | 3/2000 | Schulman et al. |
| 5,846,744 A | 12/1998 | Athey et al. | 6,049,727 A | 4/2000 | Crothall |
| 5,851,197 A | 12/1998 | Marano et al. | 6,056,718 A | 5/2000 | Funderburk et al. |
| 5,854,078 A | 12/1998 | Asher et al. | 6,063,459 A | 5/2000 | Velte |
| 5,854,189 A | 12/1998 | Kruse et al. | 6,066,243 A | 5/2000 | Anderson et al. |
| 5,856,758 A | 1/1999 | Joffe et al. | 6,067,474 A | 5/2000 | Schulman et al. |
| 5,857,967 A | 1/1999 | Frid et al. | 6,068,615 A | 5/2000 | Brown et al. |
| 5,857,983 A | 1/1999 | Douglas et al. | 6,071,249 A | 6/2000 | Cunningham et al. |
| 5,860,917 A | 1/1999 | Comanor et al. | 6,071,251 A | 6/2000 | Cunningham et al. |
| 5,872,713 A | 2/1999 | Douglas et al. | 6,071,294 A | 6/2000 | Simons et al. |
| 5,876,484 A | 3/1999 | Raskin et al. | 6,071,391 A | 6/2000 | Gotoh et al. |
| 5,879,163 A | 3/1999 | Brown et al. | 6,073,031 A | 6/2000 | Helstab et al. |
| 5,879,311 A | 3/1999 | Duchon et al. | 6,081,736 A | 6/2000 | Colvin et al. |
| 5,880,829 A | 3/1999 | Kauhaniemi et al. | 6,083,710 A | 7/2000 | Heller et al. |
| 5,882,494 A | 3/1999 | Van Antwerp | 6,088,608 A | 7/2000 | Schulman et al. |
| 5,885,211 A | 3/1999 | Eppstein et al. | 6,091,975 A | 7/2000 | Daddona et al. |
| 5,887,133 A | 3/1999 | Brown et al. | 6,091,976 A | 7/2000 | Pfeiffer et al. |
| 5,897,493 A | 4/1999 | Brown | 6,093,156 A | 7/2000 | Cunningham et al. |
| 5,898,025 A | 4/1999 | Burg et al. | 6,093,167 A | 7/2000 | Houben et al. |
| 5,899,855 A | 5/1999 | Brown | 6,093,172 A | 7/2000 | Funderburk et al. |
| 5,913,310 A | 6/1999 | Brown | 6,097,831 A | 8/2000 | Wieck et al. |
| 5,917,346 A | 6/1999 | Gord | 6,099,484 A | 8/2000 | Douglas et al. |
| 5,918,603 A | 7/1999 | Brown | 6,101,478 A | 8/2000 | Brown |
| 5,925,021 A | 7/1999 | Castellano et al. | 6,103,033 A | 8/2000 | Say et al. |
| 5,931,791 A | 8/1999 | Saltzstein et al. | 6,106,780 A | 8/2000 | Douglas et al. |
| 5,933,136 A | 8/1999 | Brown | 6,110,148 A | 8/2000 | Brown et al. |
| 5,935,224 A | 8/1999 | Svancarek et al. | 6,110,152 A | 8/2000 | Kovelman |
| 5,939,609 A | 8/1999 | Knapp et al. | 6,113,578 A | 9/2000 | Brown |
| 5,940,801 A | 8/1999 | Brown | 6,117,290 A | 9/2000 | Say et al. |
| 5,942,979 A | 8/1999 | Luppino | 6,119,028 A | 9/2000 | Schulman et al. |
| 5,945,345 A | 8/1999 | Blatt et al. | 6,120,676 A | 9/2000 | Heller et al. |
| 5,947,921 A | 9/1999 | Johnson et al. | 6,121,009 A | 9/2000 | Heller et al. |
| 5,948,512 A | 9/1999 | Kubota et al. | 6,121,611 A | 9/2000 | Lindsay et al. |
| 5,950,632 A | 9/1999 | Reber et al. | 6,122,351 A | 9/2000 | Schlueter, Jr. et al. |
| 5,951,300 A | 9/1999 | Brown | 6,125,978 A | 10/2000 | Ando et al. |

| | | | |
|---|---|---|---|
| 6,134,461 A | 10/2000 | Say et al. | |
| 6,134,504 A | 10/2000 | Douglas et al. | |
| 6,139,718 A | 10/2000 | Kurnik et al. | |
| 6,141,573 A | 10/2000 | Kurnik et al. | |
| 6,142,939 A | 11/2000 | Eppstein et al. | |
| 6,143,164 A | 11/2000 | Heller et al. | |
| 6,144,837 A | 11/2000 | Quy | |
| 6,144,869 A | 11/2000 | Berner et al. | |
| 6,144,922 A | 11/2000 | Douglas et al. | |
| 6,148,094 A | 11/2000 | Kinsella | |
| 6,150,128 A | 11/2000 | Uretsky | |
| 6,151,586 A | 11/2000 | Brown | |
| 6,153,062 A | 11/2000 | Saito et al. | |
| 6,153,069 A | 11/2000 | Pottgen et al. | |
| 6,159,147 A | 12/2000 | Lichter et al. | |
| 6,161,095 A | 12/2000 | Brown | |
| 6,162,611 A | 12/2000 | Heller et al. | |
| 6,162,639 A | 12/2000 | Douglas | |
| 6,164,284 A | 12/2000 | Schulman et al. | |
| 6,167,362 A | 12/2000 | Brown et al. | |
| 6,168,563 B1 | 1/2001 | Brown | |
| 6,170,318 B1 | 1/2001 | Lewis | |
| 6,175,752 B1 | 1/2001 | Say et al. | |
| 6,180,416 B1 | 1/2001 | Kurnik et al. | |
| 6,186,145 B1 | 2/2001 | Brown | |
| 6,192,891 B1 | 2/2001 | Gravel et al. | |
| 6,193,873 B1 | 2/2001 | Ohara et al. | |
| 6,196,970 B1 | 3/2001 | Brown | |
| 6,198,957 B1 | 3/2001 | Green | |
| 6,200,265 B1 | 3/2001 | Walsh et al. | |
| 6,201,979 B1 | 3/2001 | Kurnik et al. | |
| 6,201,980 B1 | 3/2001 | Darrow et al. | |
| 6,206,841 B1 | 3/2001 | Cunningham et al. | |
| 6,207,400 B1 | 3/2001 | Kwon | |
| 6,208,894 B1 | 3/2001 | Schulman et al. | |
| 6,210,272 B1 | 4/2001 | Brown | |
| 6,210,976 B1 | 4/2001 | Sabbadini | |
| 6,212,416 B1 | 4/2001 | Ward et al. | |
| 6,219,565 B1 | 4/2001 | Cupp et al. | |
| 6,219,574 B1 | 4/2001 | Cormier et al. | |
| 6,224,745 B1 | 5/2001 | Baltruschat | |
| 6,232,130 B1 | 5/2001 | Wolf | |
| 6,232,370 B1 | 5/2001 | Kubota et al. | |
| 6,233,471 B1 | 5/2001 | Berner et al. | |
| 6,233,539 B1 | 5/2001 | Brown | |
| 6,239,925 B1 | 5/2001 | Ardrey et al. | |
| 6,241,862 B1 | 6/2001 | McAleer et al. | |
| 6,246,330 B1 | 6/2001 | Nielsen | |
| 6,246,992 B1 | 6/2001 | Brown | |
| 6,248,065 B1 | 6/2001 | Brown | |
| 6,248,067 B1 | 6/2001 | Causey, III et al. | |
| 6,248,093 B1 | 6/2001 | Moberg | |
| 6,251,260 B1 | 6/2001 | Heller et al. | |
| 6,252,032 B1 | 6/2001 | Van Antwerp et al. | |
| 6,253,804 B1 | 7/2001 | Safabash | |
| 6,254,586 B1 | 7/2001 | Mann et al. | |
| 6,256,643 B1 | 7/2001 | Cork et al. | |
| 6,259,587 B1 | 7/2001 | Sheldon et al. | |
| 6,259,937 B1 | 7/2001 | Schulman et al. | |
| 6,260,022 B1 | 7/2001 | Brown | |
| 6,266,645 B1 | 7/2001 | Simpson | |
| 6,267,724 B1 | 7/2001 | Taylor | |
| 6,268,161 B1 | 7/2001 | Han et al. | |
| 6,270,445 B1 | 8/2001 | Dean, Jr. et al. | |
| 6,272,364 B1 | 8/2001 | Kurnik | |
| 6,275,717 B1 | 8/2001 | Gross et al. | |
| 6,280,416 B1 | 8/2001 | Van Antwerp et al. | |
| 6,280,587 B1 | 8/2001 | Matsumoto | |
| 6,281,006 B1 | 8/2001 | Heller et al. | |
| 6,283,943 B1 | 9/2001 | Dy et al. | |
| 6,284,126 B1 | 9/2001 | Kurnik et al. | |
| 6,284,478 B1 | 9/2001 | Heller et al. | |
| 6,293,925 B1 | 9/2001 | Safabash et al. | |
| 6,294,281 B1 | 9/2001 | Heller | |
| 6,295,463 B1 | 9/2001 | Stenzler | |
| 6,295,506 B1 | 9/2001 | Heinonen et al. | |
| 6,298,254 B2 | 10/2001 | Tamada | |
| 6,299,578 B1 | 10/2001 | Kurnik et al. | |
| 6,299,757 B1 | 10/2001 | Feldman et al. | |
| 6,301,499 B1 | 10/2001 | Carlson et al. | |
| 6,304,766 B1 | 10/2001 | Colvin, Jr. et al. | |
| 6,306,104 B1 | 10/2001 | Cunningham et al. | |
| 6,307,867 B1 | 10/2001 | Roobol et al. | |
| 6,309,351 B1 | 10/2001 | Kurnik et al. | |
| 6,309,884 B1 | 10/2001 | Cooper et al. | |
| 6,315,721 B2 | 11/2001 | Schulman et al. | |
| 6,319,540 B1 | 11/2001 | Van Antwerp et al. | |
| 6,326,160 B1 | 12/2001 | Dunn et al. | |
| 6,329,161 B1 | 12/2001 | Heller et al. | |
| 6,329,929 B1 | 12/2001 | Weijand et al. | |
| 6,330,426 B2 | 12/2001 | Brown et al. | |
| 6,330,464 B1 | 12/2001 | Colvin, Jr. et al. | |
| 6,331,518 B2 | 12/2001 | Hemm et al. | |
| 6,334,778 B1 | 1/2002 | Brown | |
| 6,336,900 B1 | 1/2002 | Alleckson et al. | |
| 6,338,790 B1 | 1/2002 | Feldman et al. | |
| 6,340,421 B1 | 1/2002 | Vachon et al. | |
| 6,341,232 B1 | 1/2002 | Conn et al. | |
| 6,356,776 B1 | 3/2002 | Berner et al. | |
| 6,360,888 B1 | 3/2002 | McIvor et al. | |
| 6,366,793 B1 | 4/2002 | Bell et al. | |
| 6,366,794 B1 | 4/2002 | Moussy et al. | |
| 6,368,141 B1 | 4/2002 | Van Antwerp et al. | |
| 6,368,274 B1 | 4/2002 | Van Antwerp et al. | |
| 6,370,410 B2 | 4/2002 | Kurnik et al. | |
| 6,377,828 B1 | 4/2002 | Chaiken et al. | |
| 6,379,301 B1 | 4/2002 | Worthington et al. | |
| 6,383,767 B1 | 5/2002 | Polak | |
| 6,387,048 B1 | 5/2002 | Schulman et al. | |
| 6,391,643 B1 | 5/2002 | Chen et al. | |
| 6,393,318 B1 | 5/2002 | Conn et al. | |
| 6,398,562 B1 | 6/2002 | Butler et al. | |
| 6,405,066 B1 | 6/2002 | Essenpreis et al. | |
| 6,413,393 B1 | 7/2002 | Van Antwerp et al. | |
| 6,416,471 B1 | 7/2002 | Kumar et al. | |
| 6,418,332 B1 | 7/2002 | Mastrototaro et al. | |
| 6,424,847 B1 | 7/2002 | Mastrototaro et al. | |
| 6,427,088 B1 | 7/2002 | Bowman, IV et al. | |
| 6,434,409 B1 | 8/2002 | Pfeiffer et al. | |
| 6,438,414 B1 | 8/2002 | Conn et al. | |
| 6,440,068 B1 | 8/2002 | Brown et al. | |
| 6,442,637 B1 | 8/2002 | Hawkins et al. | |
| 6,443,942 B2 | 9/2002 | Van Antwerp et al. | |
| 6,454,710 B1 | 9/2002 | Ballerstadt et al. | |
| 6,462,162 B2 | 10/2002 | Van Antwerp et al. | |
| 6,464,848 B1 | 10/2002 | Matsumoto | |
| 6,466,810 B1 | 10/2002 | Ward et al. | |
| 6,468,222 B1 | 10/2002 | Mault et al. | |
| 6,472,122 B1 | 10/2002 | Schulman et al. | |
| 6,475,750 B1 | 11/2002 | Han et al. | |
| 6,477,395 B2 | 11/2002 | Schulman et al. | |
| 6,478,736 B1 | 11/2002 | Mault | |
| 6,480,730 B2 | 11/2002 | Darrow et al. | |
| 6,482,156 B2 | 11/2002 | Iliff | |
| 6,482,158 B2 | 11/2002 | Mault | |
| 6,482,604 B2 | 11/2002 | Kwon | |
| 6,484,045 B1 | 11/2002 | Holker et al. | |
| 6,484,046 B1 | 11/2002 | Say et al. | |
| 6,485,138 B1 | 11/2002 | Kubota et al. | |
| 6,494,830 B1 | 12/2002 | Wessel | |
| 6,496,728 B2 | 12/2002 | Li et al. | |
| 6,505,059 B1 | 1/2003 | Kollias et al. | |
| 6,512,939 B1 | 1/2003 | Colvin et al. | |
| 6,513,532 B2 | 2/2003 | Mault et al. | |
| 6,514,718 B2 | 2/2003 | Heller et al. | |
| 6,515,593 B1 | 2/2003 | Stark et al. | |
| 6,520,326 B2 | 2/2003 | McIvor et al. | |
| 6,529,755 B2 | 3/2003 | Kurnik et al. | |
| 6,529,772 B2 | 3/2003 | Carlson et al. | |
| 6,530,915 B1 | 3/2003 | Eppstein et al. | |
| 6,534,322 B1 | 3/2003 | Sabbadini | |
| 6,534,323 B1 | 3/2003 | Sabbadini | |
| 6,535,753 B1 | 3/2003 | Raskas | |
| 6,537,243 B1 | 3/2003 | Henning et al. | |
| 6,540,675 B2 | 4/2003 | Aceti et al. | |
| 6,544,212 B2 | 4/2003 | Galley et al. | |
| 6,546,269 B1 | 4/2003 | Kurnik | |
| 6,549,796 B2 | 4/2003 | Sohrab | |

| | | | | | | |
|---|---|---|---|---|---|---|
| 6,551,276 B1 | 4/2003 | Mann et al. | | 6,741,163 B1 | 5/2004 | Roberts |
| 6,551,494 B1 | 4/2003 | Heller et al. | | 6,741,876 B1 | 5/2004 | Scecina et al. |
| 6,553,244 B2 | 4/2003 | Lesho et al. | | 6,741,877 B1 | 5/2004 | Shults et al. |
| 6,554,798 B1 | 4/2003 | Mann et al. | | 6,744,350 B2 | 6/2004 | Blomquist |
| 6,558,320 B1 | 5/2003 | Causey, III et al. | | 6,749,587 B2 | 6/2004 | Flaherty |
| 6,558,321 B1 | 5/2003 | Burd et al. | | 6,750,311 B1 | 6/2004 | Van Antwerp et al. |
| 6,558,351 B1 | 5/2003 | Steil et al. | | 6,758,810 B2 | 7/2004 | Lebel et al. |
| 6,560,471 B1 | 5/2003 | Heller et al. | | 6,766,183 B2 | 7/2004 | Walsh et al. |
| 6,561,978 B1 | 5/2003 | Conn et al. | | 6,766,201 B2 | 7/2004 | Von Arx et al. |
| 6,562,001 B2 | 5/2003 | Lebel et al. | | 6,768,425 B2 | 7/2004 | Flaherty et al. |
| 6,564,105 B2 | 5/2003 | Starkweather et al. | | 6,770,030 B1 | 8/2004 | Schaupp et al. |
| 6,565,509 B1 | 5/2003 | Say et al. | | 6,770,729 B2 | 8/2004 | Van Antwerp |
| 6,571,128 B2 | 5/2003 | Lebel et al. | | 6,771,995 B2 | 8/2004 | Kurnik et al. |
| 6,571,200 B1 | 5/2003 | Mault | | 6,773,563 B2 | 8/2004 | Matsumoto |
| 6,576,101 B1 | 6/2003 | Heller et al. | | 6,780,156 B2 | 8/2004 | Haueter et al. |
| 6,576,117 B1 | 6/2003 | Iketaki et al. | | 6,780,297 B2 | 8/2004 | Matsumoto et al. |
| 6,577,899 B2 | 6/2003 | Lebel et al. | | 6,780,871 B2 | 8/2004 | Glick et al. |
| 6,579,498 B1 | 6/2003 | Eglise | | 6,784,274 B2 | 8/2004 | Van Antwerp et al. |
| 6,579,690 B1 | 6/2003 | Bonnecaze et al. | | 6,790,178 B1 | 9/2004 | Mault et al. |
| 6,584,335 B1 | 6/2003 | Haar et al. | | 6,794,195 B2 | 9/2004 | Colvin, Jr. |
| 6,585,644 B2 | 7/2003 | Lebel et al. | | 6,800,451 B2 | 10/2004 | Daniloff et al. |
| 6,587,705 B1 | 7/2003 | Kim et al. | | 6,804,544 B2 | 10/2004 | Van Antwerp et al. |
| 6,591,125 B1 | 7/2003 | Buse et al. | | 6,809,507 B2 | 10/2004 | Morgan et al. |
| 6,591,126 B2 | 7/2003 | Roeper et al. | | 6,809,653 B1 | 10/2004 | Mann et al. |
| 6,594,514 B2 | 7/2003 | Berner et al. | | 6,810,290 B2 | 10/2004 | Lebel et al. |
| 6,595,919 B2 | 7/2003 | Berner et al. | | 6,811,533 B2 | 11/2004 | Lebel et al. |
| 6,595,929 B2 | 7/2003 | Stivoric et al. | | 6,811,534 B2 | 11/2004 | Bowman, IV et al. |
| 6,602,678 B2 | 8/2003 | Kwon et al. | | 6,811,659 B2 | 11/2004 | Vachon |
| 6,602,909 B1 | 8/2003 | Jarowski | | 6,812,031 B1 | 11/2004 | Carlsson |
| 6,605,200 B1 | 8/2003 | Mao et al. | | 6,813,519 B2 | 11/2004 | Lebel et al. |
| 6,605,201 B1 | 8/2003 | Mao et al. | | 6,816,742 B2 | 11/2004 | Kim et al. |
| 6,607,509 B2 | 8/2003 | Bobroff et al. | | 6,835,553 B2 | 12/2004 | Han et al. |
| 6,608,562 B1 | 8/2003 | Kimura et al. | | RE38,681 E | 1/2005 | Kurnik et al. |
| 6,610,012 B2 | 8/2003 | Mault | | 6,840,912 B2 | 1/2005 | Kloepfer et al. |
| 6,612,306 B1 | 9/2003 | Mault | | 6,844,023 B2 | 1/2005 | Schulman et al. |
| 6,615,078 B1 | 9/2003 | Burson et al. | | 6,849,237 B2 | 2/2005 | Housefield et al. |
| 6,616,613 B1 | 9/2003 | Goodman | | 6,850,790 B2 | 2/2005 | Berner et al. |
| 6,618,603 B2 | 9/2003 | Varalli et al. | | 6,852,104 B2 | 2/2005 | Blomquist |
| 6,620,106 B2 | 9/2003 | Mault | | 6,852,500 B1 | 2/2005 | Hoss et al. |
| 6,627,058 B1 | 9/2003 | Chan | | 6,852,694 B2 | 2/2005 | Van Antwerp et al. |
| 6,629,934 B2 | 10/2003 | Mault et al. | | 6,853,854 B1 | 2/2005 | Proniewicz et al. |
| 6,633,772 B2 | 10/2003 | Ford et al. | | 6,856,928 B2 | 2/2005 | Harmon |
| 6,635,014 B2 | 10/2003 | Starkweather et al. | | 6,858,403 B2 | 2/2005 | Han et al. |
| 6,641,533 B2 | 11/2003 | Causey, III et al. | | 6,862,465 B2 | 3/2005 | Shults et al. |
| 6,642,015 B2 | 11/2003 | Vachon et al. | | 6,862,466 B2 | 3/2005 | Ackerman |
| 6,645,142 B2 | 11/2003 | Braig et al. | | 6,872,200 B2 | 3/2005 | Mann et al. |
| 6,645,368 B1 | 11/2003 | Beaty et al. | | 6,873,268 B2 | 3/2005 | Lebel et al. |
| 6,648,821 B2 | 11/2003 | Lebel et al. | | 6,881,551 B2 | 4/2005 | Heller et al. |
| 6,653,091 B1 | 11/2003 | Dunn et al. | | 6,882,940 B2 | 4/2005 | Potts et al. |
| 6,654,625 B1 | 11/2003 | Say et al. | | 6,885,883 B2 | 4/2005 | Parris et al. |
| 6,659,948 B2 | 12/2003 | Lebel et al. | | 6,892,085 B2 | 5/2005 | McIvor et al. |
| 6,668,196 B1 | 12/2003 | Villegas et al. | | 6,895,263 B2 | 5/2005 | Shin et al. |
| 6,671,554 B2 | 12/2003 | Gibson et al. | | 6,895,265 B2 | 5/2005 | Silver |
| 6,673,625 B2 | 1/2004 | Satcher, Jr. et al. | | 6,899,683 B2 | 5/2005 | Mault et al. |
| 6,682,938 B1 | 1/2004 | Satcher, Jr. et al. | | 6,899,684 B2 | 5/2005 | Mault et al. |
| 6,683,040 B2 | 1/2004 | Bragulla et al. | | 6,902,207 B2 | 6/2005 | Lickliter |
| 6,687,522 B2 | 2/2004 | Tamada | | 6,902,905 B2 | 6/2005 | Burson et al. |
| 6,687,546 B2 | 2/2004 | Lebel et al. | | 6,904,301 B2 | 6/2005 | Raskas |
| 6,689,056 B1 | 2/2004 | Kilcoyne et al. | | 6,907,127 B1 | 6/2005 | Kravitz et al. |
| 6,690,276 B1 | 2/2004 | Marino | | 6,915,147 B2 | 7/2005 | Lebel et al. |
| 6,693,069 B2 | 2/2004 | Korber et al. | | 6,918,874 B1 | 7/2005 | Hatch et al. |
| 6,694,158 B2 | 2/2004 | Polak | | 6,922,578 B2 | 7/2005 | Eppstein et al. |
| 6,694,191 B2 | 2/2004 | Starkweather et al. | | RE38,775 E | 8/2005 | Kurnik et al. |
| 6,695,860 B1 | 2/2004 | Ward et al. | | 6,923,764 B2 | 8/2005 | Aceti et al. |
| 6,698,269 B2 | 3/2004 | Baber et al. | | 6,923,936 B2 | 8/2005 | Swanson et al. |
| 6,701,270 B1 | 3/2004 | Miller et al. | | 6,927,246 B2 | 8/2005 | Noronha et al. |
| 6,702,857 B2 | 3/2004 | Brauker et al. | | 6,931,327 B2 | 8/2005 | Goode, Jr. et al. |
| 6,704,587 B1 | 3/2004 | Kumar et al. | | 6,932,894 B2 | 8/2005 | Mao et al. |
| 6,711,423 B2 | 3/2004 | Colvin, Jr. | | 6,936,006 B2 | 8/2005 | Sabra |
| 6,723,046 B2 | 4/2004 | Lichtenstein et al. | | 6,936,029 B2 | 8/2005 | Mann et al. |
| 6,728,560 B2 | 4/2004 | Kollias et al. | | 6,940,590 B2 | 9/2005 | Colvin, Jr. et al. |
| 6,731,976 B2 | 5/2004 | Penn et al. | | 6,941,163 B2 | 9/2005 | Ford et al. |
| 6,733,446 B2 | 5/2004 | Lebel et al. | | 6,950,708 B2 | 9/2005 | Bowman, IV et al. |
| 6,734,162 B2 | 5/2004 | Van Antwerp et al. | | 6,952,603 B2 | 10/2005 | Gerber et al. |
| 6,736,777 B2 | 5/2004 | Kim et al. | | 6,954,673 B2 | 10/2005 | Von Arx et al. |
| 6,736,797 B1 | 5/2004 | Larsen et al. | | 6,955,650 B2 | 10/2005 | Mault et al. |
| 6,737,401 B2 | 5/2004 | Kim et al. | | 6,957,102 B2 | 10/2005 | Silver et al. |
| 6,738,654 B2 | 5/2004 | Sohrab | | 6,957,107 B2 | 10/2005 | Rogers et al. |
| 6,740,075 B2 | 5/2004 | Lebel et al. | | 6,958,705 B2 | 10/2005 | Lebel et al. |

| | | | | | | |
|---|---|---|---|---|---|---|
| 6,968,294 B2 | 11/2005 | Gutta et al. | 7,424,318 B2 | 9/2008 | Brister et al. |
| 6,968,375 B1 | 11/2005 | Brown | 7,460,898 B2 | 12/2008 | Brister et al. |
| 6,971,274 B2 | 12/2005 | Olin | 7,467,003 B2 | 12/2008 | Brister et al. |
| 6,974,437 B2 | 12/2005 | Lebel et al. | 7,471,972 B2 | 12/2008 | Rhodes et al. |
| 6,978,182 B2 | 12/2005 | Mazar et al. | 7,494,465 B2 | 2/2009 | Brister et al. |
| 6,979,326 B2 | 12/2005 | Mann et al. | 7,497,827 B2 | 3/2009 | Brister et al. |
| 6,985,870 B2 | 1/2006 | Martucci et al. | 7,519,408 B2 | 4/2009 | Rasdal et al. |
| 6,990,366 B2 | 1/2006 | Say et al. | 7,547,281 B2 | 6/2009 | Hayes et al. |
| 6,991,096 B2 | 1/2006 | Gottlieb et al. | 7,569,030 B2 | 8/2009 | Lebel et al. |
| 6,997,907 B2 | 2/2006 | Safabash et al. | 7,583,990 B2 | 9/2009 | Goode, Jr. et al. |
| 6,997,920 B2 | 2/2006 | Mann et al. | 7,591,801 B2 | 9/2009 | Brauker et al. |
| 6,998,247 B2 | 2/2006 | Monfre et al. | 7,599,726 B2 | 10/2009 | Goode, Jr. et al. |
| 6,999,810 B2 | 2/2006 | Berner et al. | 7,613,491 B2 | 11/2009 | Boock et al. |
| 7,003,336 B2 | 2/2006 | Holker et al. | 7,615,007 B2 | 11/2009 | Shults et al. |
| 7,003,340 B2 | 2/2006 | Say et al. | 7,618,369 B2 | 11/2009 | Hayter et al. |
| 7,003,341 B2 | 2/2006 | Say et al. | 7,632,228 B2 | 12/2009 | Brauker et al. |
| 7,004,901 B2 | 2/2006 | Fish | 7,637,868 B2 | 12/2009 | Saint et al. |
| 7,005,857 B2 | 2/2006 | Stiene et al. | 7,640,048 B2 | 12/2009 | Dobbles et al. |
| 7,011,630 B2 | 3/2006 | Desai et al. | 7,651,596 B2 | 1/2010 | Petisce et al. |
| 7,018,366 B2 | 3/2006 | Easter | 7,654,956 B2 | 2/2010 | Brister et al. |
| 7,018,568 B2 | 3/2006 | Tierney | 7,657,297 B2 | 2/2010 | Simpson et al. |
| 7,022,072 B2 | 4/2006 | Fox et al. | 7,711,402 B2 | 5/2010 | Shults et al. |
| 7,024,236 B2 | 4/2006 | Ford et al. | 7,713,574 B2 | 5/2010 | Brister et al. |
| 7,024,245 B2 | 4/2006 | Lebel et al. | 7,715,893 B2 | 5/2010 | Kamath et al. |
| 7,025,743 B2 | 4/2006 | Mann et al. | 7,813,809 B2 | 10/2010 | Strother et al. |
| 7,029,444 B2 | 4/2006 | Shin et al. | 2001/0011224 A1 | 8/2001 | Brown |
| 7,039,810 B1 | 5/2006 | Nichols | 2001/0016310 A1 | 8/2001 | Brown et al. |
| 7,041,468 B2 * | 5/2006 | Drucker et al. .................. 435/14 | 2001/0016682 A1 | 8/2001 | Berner et al. |
| 7,049,277 B2 | 5/2006 | Bragulla et al. | 2001/0016683 A1 | 8/2001 | Darrow et al. |
| 7,052,251 B2 | 5/2006 | Nason et al. | 2001/0020124 A1 | 9/2001 | Tamada |
| 7,052,472 B1 | 5/2006 | Miller et al. | 2001/0029340 A1 | 10/2001 | Mault et al. |
| 7,052,483 B2 | 5/2006 | Wojcik | 2001/0032278 A1 | 10/2001 | Brown et al. |
| 7,056,302 B2 | 6/2006 | Douglas | 2001/0037060 A1 | 11/2001 | Thompson et al. |
| 7,074,307 B2 | 7/2006 | Simpson et al. | 2001/0037069 A1 | 11/2001 | Carlson et al. |
| 7,079,977 B2 | 7/2006 | Osorio et al. | 2001/0039504 A1 | 11/2001 | Linberg et al. |
| 7,081,195 B2 | 7/2006 | Simpson et al. | 2001/0041830 A1 | 11/2001 | Varalli et al. |
| 7,089,780 B2 | 8/2006 | Sunshine et al. | 2001/0041831 A1 | 11/2001 | Starkweather et al. |
| 7,098,803 B2 | 8/2006 | Mann et al. | 2001/0044581 A1 | 11/2001 | Mault |
| 7,108,778 B2 | 9/2006 | Simpson et al. | 2001/0044588 A1 | 11/2001 | Mault |
| 7,110,803 B2 | 9/2006 | Shults et al. | 2001/0047125 A1 | 11/2001 | Quy |
| 7,113,821 B1 | 9/2006 | Sun et al. | 2001/0049096 A1 | 12/2001 | Brown |
| 7,114,502 B2 | 10/2006 | Schulman et al. | 2001/0049470 A1 | 12/2001 | Mault et al. |
| 7,125,382 B2 | 10/2006 | Zhou et al. | 2002/0002326 A1 | 1/2002 | Causey, III et al. |
| 7,133,710 B2 | 11/2006 | Acosta et al. | 2002/0002328 A1 | 1/2002 | Tamada |
| 7,134,999 B2 | 11/2006 | Brauker et al. | 2002/0004640 A1 | 1/2002 | Conn et al. |
| 7,136,689 B2 | 11/2006 | Shults et al. | 2002/0010414 A1 | 1/2002 | Coston et al. |
| 7,150,975 B2 | 12/2006 | Tamada et al. | 2002/0016530 A1 | 2/2002 | Brown |
| 7,155,112 B2 | 12/2006 | Uno et al. | 2002/0016719 A1 | 2/2002 | Nemeth et al. |
| 7,163,511 B2 | 1/2007 | Conn et al. | 2002/0019022 A1 | 2/2002 | Dunn et al. |
| 7,171,274 B2 | 1/2007 | Starkweather et al. | 2002/0019586 A1 | 2/2002 | Teller et al. |
| 7,183,068 B2 | 2/2007 | Burson et al. | 2002/0019748 A1 | 2/2002 | Brown |
| 7,183,102 B2 | 2/2007 | Monfre et al. | 2002/0026937 A1 | 3/2002 | Mault |
| 7,189,341 B2 | 3/2007 | Li et al. | 2002/0027164 A1 | 3/2002 | Mault et al. |
| 7,190,988 B2 | 3/2007 | Say et al. | 2002/0028995 A1 | 3/2002 | Mault |
| 7,192,450 B2 | 3/2007 | Brauker et al. | 2002/0040208 A1 | 4/2002 | Flaherty et al. |
| 7,198,606 B2 | 4/2007 | Boecker et al. | 2002/0042090 A1 | 4/2002 | Heller et al. |
| 7,221,977 B1 | 5/2007 | Weaver et al. | 2002/0047867 A1 | 4/2002 | Mault et al. |
| 7,226,442 B2 | 6/2007 | Sheppard et al. | 2002/0053637 A1 | 5/2002 | Conn et al. |
| 7,226,978 B2 | 6/2007 | Tapsak et al. | 2002/0062069 A1 | 5/2002 | Mault |
| 7,228,163 B2 | 6/2007 | Ackerman | 2002/0063060 A1 | 5/2002 | Gascoyne et al. |
| 7,233,817 B2 | 6/2007 | Yen | 2002/0068858 A1 | 6/2002 | Braig et al. |
| 7,241,266 B2 | 7/2007 | Zhou et al. | 2002/0072784 A1 | 6/2002 | Sheppard et al. |
| 7,261,691 B1 | 8/2007 | Asomani | 2002/0072858 A1 | 6/2002 | Cheng |
| 7,267,665 B2 | 9/2007 | Steil et al. | 2002/0077765 A1 | 6/2002 | Mault |
| 7,276,029 B2 | 10/2007 | Goode, Jr. et al. | 2002/0077766 A1 | 6/2002 | Mault |
| 7,278,983 B2 | 10/2007 | Ireland et al. | 2002/0081559 A1 | 6/2002 | Brown et al. |
| 7,291,107 B2 | 11/2007 | Hellwig et al. | 2002/0083461 A1 | 6/2002 | Hutcheson et al. |
| 7,295,867 B2 | 11/2007 | Berner et al. | 2002/0087056 A1 | 7/2002 | Aceti et al. |
| 7,297,112 B2 | 11/2007 | Zhou et al. | 2002/0091312 A1 | 7/2002 | Berner et al. |
| 7,299,082 B2 | 11/2007 | Feldman et al. | 2002/0103425 A1 | 8/2002 | Mault |
| 7,310,544 B2 | 12/2007 | Brister et al. | 2002/0103499 A1 | 8/2002 | Perez et al. |
| 7,324,012 B2 | 1/2008 | Mann et al. | 2002/0106709 A1 | 8/2002 | Potts et al. |
| 7,335,294 B2 | 2/2008 | Heller et al. | 2002/0107433 A1 | 8/2002 | Mault |
| 7,354,420 B2 | 4/2008 | Steil et al. | 2002/0107476 A1 | 8/2002 | Mann et al. |
| 7,364,592 B2 | 4/2008 | Carr-Brendel et al. | 2002/0109600 A1 | 8/2002 | Mault et al. |
| 7,366,556 B2 | 4/2008 | Brister et al. | 2002/0119711 A1 | 8/2002 | VanAntwerp et al. |
| 7,379,765 B2 | 5/2008 | Petisce et al. | 2002/0124017 A1 | 9/2002 | Mault |
| 7,398,183 B2 | 7/2008 | Holland et al. | 2002/0126036 A1 | 9/2002 | Flaherty et al. |
| 7,402,153 B2 | 7/2008 | Steil et al. | 2002/0128594 A1 | 9/2002 | Das et al. |

| | | | | | |
|---|---|---|---|---|---|
| 2002/0130042 A1 | 9/2002 | Moerman et al. | 2004/0054263 A1 | 3/2004 | Moerman et al. |
| 2002/0133378 A1 | 9/2002 | Mault et al. | 2004/0059201 A1 | 3/2004 | Ginsberg |
| 2002/0147135 A1 | 10/2002 | Schnell | 2004/0064068 A1 | 4/2004 | DeNuzzio et al. |
| 2002/0161286 A1 | 10/2002 | Gerber et al. | 2004/0069164 A1 | 4/2004 | Nakamura et al. |
| 2002/0161288 A1 | 10/2002 | Shin et al. | 2004/0072357 A1 | 4/2004 | Stiene et al. |
| 2002/0169394 A1 | 11/2002 | Eppstein et al. | 2004/0073095 A1 | 4/2004 | Causey, III et al. |
| 2002/0169635 A1 | 11/2002 | Shillingburg | 2004/0096959 A1 | 5/2004 | Stiene et al. |
| 2002/0177764 A1 | 11/2002 | Sohrab | 2004/0106858 A1 | 6/2004 | Say et al. |
| 2002/0193679 A1 | 12/2002 | Malave et al. | 2004/0108226 A1 | 6/2004 | Polychronakos et al. |
| 2003/0004403 A1 | 1/2003 | Drinan et al. | 2004/0122353 A1 | 6/2004 | Shahmirian et al. |
| 2003/0023182 A1 | 1/2003 | Mault et al. | 2004/0122489 A1 | 6/2004 | Mazar et al. |
| 2003/0023317 A1 | 1/2003 | Brauker et al. | 2004/0122530 A1 | 6/2004 | Hansen et al. |
| 2003/0028089 A1 | 2/2003 | Galley et al. | 2004/0133164 A1 | 7/2004 | Funderburk et al. |
| 2003/0028120 A1 | 2/2003 | Mault et al. | 2004/0138588 A1 | 7/2004 | Saikley et al. |
| 2003/0032077 A1 | 2/2003 | Itoh et al. | 2004/0146909 A1 | 7/2004 | Duong et al. |
| 2003/0032867 A1 | 2/2003 | Crothall et al. | 2004/0152622 A1 | 8/2004 | Keith et al. |
| 2003/0032868 A1 | 2/2003 | Graskov et al. | 2004/0152961 A1 | 8/2004 | Carlson et al. |
| 2003/0032874 A1 | 2/2003 | Rhodes et al. | 2004/0153585 A1 | 8/2004 | Kawatahara et al. |
| 2003/0040683 A1 | 2/2003 | Rule et al. | 2004/0162473 A1 | 8/2004 | Sohrab |
| 2003/0042137 A1 | 3/2003 | Mao et al. | 2004/0164961 A1 | 8/2004 | Bal et al. |
| 2003/0050537 A1 | 3/2003 | Wessel | 2004/0167383 A1 | 8/2004 | Kim et al. |
| 2003/0050546 A1 | 3/2003 | Desai et al. | 2004/0167464 A1 * | 8/2004 | Ireland et al. .................. 604/66 |
| 2003/0065257 A1 | 4/2003 | Mault et al. | 2004/0167801 A1 | 8/2004 | Say et al. |
| 2003/0065273 A1 | 4/2003 | Mault et al. | 2004/0171921 A1 | 9/2004 | Say et al. |
| 2003/0065274 A1 | 4/2003 | Mault et al. | 2004/0172284 A1 | 9/2004 | Sullivan et al. |
| 2003/0065275 A1 | 4/2003 | Mault et al. | 2004/0176672 A1 | 9/2004 | Silver et al. |
| 2003/0065308 A1 | 4/2003 | Lebel et al. | 2004/0176913 A1 | 9/2004 | Kawatahara et al. |
| 2003/0081370 A1 | 5/2003 | Haskell et al. | 2004/0186362 A1 | 9/2004 | Brauker et al. |
| 2003/0100040 A1 | 5/2003 | Bonnecaze et al. | 2004/0186365 A1 | 9/2004 | Jin et al. |
| 2003/0100821 A1 | 5/2003 | Heller et al. | 2004/0193025 A1 | 9/2004 | Steil et al. |
| 2003/0105407 A1 | 6/2003 | Pearce et al. | 2004/0193090 A1 | 9/2004 | Lebel et al. |
| 2003/0108976 A1 | 6/2003 | Braig et al. | 2004/0197846 A1 | 10/2004 | Hockersmith et al. |
| 2003/0122021 A1 | 7/2003 | McConnell et al. | 2004/0199059 A1 | 10/2004 | Brauker et al. |
| 2003/0125612 A1 | 7/2003 | Fox et al. | 2004/0202576 A1 | 10/2004 | Aceti et al. |
| 2003/0130616 A1 | 7/2003 | Steil et al. | 2004/0204687 A1 | 10/2004 | Mogensen et al. |
| 2003/0134347 A1 | 7/2003 | Heller et al. | 2004/0208780 A1 | 10/2004 | Faries, Jr. et al. |
| 2003/0135100 A1 | 7/2003 | Kim et al. | 2004/0225338 A1 | 11/2004 | Lebel et al. |
| 2003/0135333 A1 | 7/2003 | Aceti et al. | 2004/0235446 A1 | 11/2004 | Flaherty et al. |
| 2003/0146841 A1 | 8/2003 | Koenig | 2004/0236200 A1 | 11/2004 | Say et al. |
| 2003/0153820 A1 | 8/2003 | Berner et al. | 2004/0248204 A1 | 12/2004 | Moerman |
| 2003/0153821 A1 | 8/2003 | Berner et al. | 2004/0249250 A1 | 12/2004 | McGee et al. |
| 2003/0158472 A1 | 8/2003 | Sohrab | 2004/0249253 A1 | 12/2004 | Racchini et al. |
| 2003/0158707 A1 | 8/2003 | Doi | 2004/0249254 A1 | 12/2004 | Racchini et al. |
| 2003/0168338 A1 | 9/2003 | Gao et al. | 2004/0249999 A1 | 12/2004 | Connolly et al. |
| 2003/0175806 A1 | 9/2003 | Rule et al. | 2004/0253736 A1 | 12/2004 | Stout et al. |
| 2003/0176183 A1 | 9/2003 | Drucker et al. | 2004/0254429 A1 | 12/2004 | Yang |
| 2003/0176933 A1 | 9/2003 | Lebel et al. | 2004/0254433 A1 | 12/2004 | Bandis et al. |
| 2003/0181851 A1 | 9/2003 | Mann et al. | 2004/0254434 A1 | 12/2004 | Goodnow et al. |
| 2003/0181852 A1 | 9/2003 | Mann et al. | 2004/0260363 A1 | 12/2004 | Von Arx et al. |
| 2003/0187338 A1 | 10/2003 | Say et al. | 2004/0263354 A1 | 12/2004 | Mann et al. |
| 2003/0187525 A1 | 10/2003 | Mann et al. | 2004/0267300 A1 | 12/2004 | Mace |
| 2003/0191376 A1 | 10/2003 | Samuels et al. | 2005/0003470 A1 | 1/2005 | Nelson et al. |
| 2003/0191431 A1 | 10/2003 | Mann et al. | 2005/0004439 A1 | 1/2005 | Shin et al. |
| 2003/0195403 A1 | 10/2003 | Berner et al. | 2005/0004494 A1 | 1/2005 | Perez et al. |
| 2003/0195462 A1 | 10/2003 | Mann et al. | 2005/0010087 A1 | 1/2005 | Banet et al. |
| 2003/0199790 A1 | 10/2003 | Boecker et al. | 2005/0010269 A1 | 1/2005 | Lebel et al. |
| 2003/0199791 A1 | 10/2003 | Boecker et al. | 2005/0016276 A1 | 1/2005 | Guan et al. |
| 2003/0199903 A1 | 10/2003 | Boecker et al. | 2005/0027177 A1 | 2/2005 | Shin et al. |
| 2003/0203498 A1 | 10/2003 | Neel et al. | 2005/0027179 A1 | 2/2005 | Berner et al. |
| 2003/0208110 A1 | 11/2003 | Mault et al. | 2005/0027180 A1 | 2/2005 | Goode, Jr. et al. |
| 2003/0208113 A1 | 11/2003 | Mault et al. | 2005/0027181 A1 | 2/2005 | Goode, Jr. et al. |
| 2003/0208133 A1 | 11/2003 | Mault | 2005/0027462 A1 | 2/2005 | Goode, Jr. et al. |
| 2003/0208409 A1 | 11/2003 | Mault | 2005/0027463 A1 | 2/2005 | Goode, Jr. et al. |
| 2003/0212317 A1 | 11/2003 | Kovatchev et al. | 2005/0031689 A1 | 2/2005 | Shults et al. |
| 2003/0212364 A1 | 11/2003 | Mann et al. | 2005/0033132 A1 | 2/2005 | Shults et al. |
| 2003/0212379 A1 | 11/2003 | Bylund et al. | 2005/0038332 A1 | 2/2005 | Saidara et al. |
| 2003/0216630 A1 | 11/2003 | Jersey-Willuhn et al. | 2005/0038680 A1 | 2/2005 | McMahon |
| 2003/0217966 A1 | 11/2003 | Tapsak et al. | 2005/0043598 A1 | 2/2005 | Goode, Jr. et al. |
| 2003/0226695 A1 | 12/2003 | Mault | 2005/0043894 A1 | 2/2005 | Fernandez |
| 2003/0229514 A2 | 12/2003 | Brown | 2005/0049473 A1 | 3/2005 | Desai et al. |
| 2003/0232370 A1 | 12/2003 | Trifiro | 2005/0054909 A1 | 3/2005 | Petisce et al. |
| 2003/0235817 A1 | 12/2003 | Bartkowiak et al. | 2005/0065464 A1 | 3/2005 | Talbot et al. |
| 2004/0010207 A1 | 1/2004 | Flaherty et al. | 2005/0090607 A1 | 4/2005 | Tapsak et al. |
| 2004/0011671 A1 | 1/2004 | Shults et al. | 2005/0096511 A1 | 5/2005 | Fox et al. |
| 2004/0018486 A1 | 1/2004 | Dunn et al. | 2005/0096512 A1 | 5/2005 | Fox et al. |
| 2004/0039256 A1 | 2/2004 | Kawatahara et al. | 2005/0112169 A1 | 5/2005 | Brauker et al. |
| 2004/0039298 A1 | 2/2004 | Abreu | 2005/0112544 A1 | 5/2005 | Xu et al. |
| 2004/0040840 A1 | 3/2004 | Mao et al. | 2005/0113653 A1 | 5/2005 | Fox et al. |
| 2004/0045879 A1 | 3/2004 | Shults et al. | 2005/0113657 A1 | 5/2005 | Alarcon et al. |

| | | | | | |
|---|---|---|---|---|---|
| 2005/0113658 A1 | 5/2005 | Jacobson et al. | 2006/0052679 A1 | 3/2006 | Kotulla et al. |
| 2005/0113886 A1 | 5/2005 | Fischell et al. | 2006/0058602 A1 | 3/2006 | Kwiatkowski et al. |
| 2005/0114068 A1 | 5/2005 | Chey et al. | 2006/0063218 A1 | 3/2006 | Bartkowiak et al. |
| 2005/0118726 A1 | 6/2005 | Schultz et al. | 2006/0074564 A1 | 4/2006 | Bartkowiak et al. |
| 2005/0121322 A1 | 6/2005 | Say et al. | 2006/0142651 A1 | 6/2006 | Brister et al. |
| 2005/0124873 A1 | 6/2005 | Shults et al. | 2006/0155180 A1 | 7/2006 | Brister et al. |
| 2005/0131346 A1 | 6/2005 | Douglas | 2006/0166629 A1 | 7/2006 | Reggiardo |
| 2005/0137471 A1 | 6/2005 | Haar et al. | 2006/0173260 A1 | 8/2006 | Gaoni et al. |
| 2005/0143635 A1 | 6/2005 | Kamath et al. | 2006/0173406 A1 | 8/2006 | Hayes et al. |
| 2005/0143636 A1 | 6/2005 | Zhang et al. | 2006/0173444 A1 | 8/2006 | Choy et al. |
| 2005/0148003 A1 | 7/2005 | Keith et al. | 2006/0183985 A1 | 8/2006 | Brister et al. |
| 2005/0154271 A1 | 7/2005 | Rasdal et al. | 2006/0189863 A1 | 8/2006 | Peyser et al. |
| 2005/0161346 A1 | 7/2005 | Simpson et al. | 2006/0195029 A1 | 8/2006 | Shults et al. |
| 2005/0171503 A1 | 8/2005 | Van Den Berghe et al. | 2006/0200112 A1 | 9/2006 | Paul |
| 2005/0171513 A1 | 8/2005 | Mann et al. | 2006/0222566 A1 | 10/2006 | Brauker et al. |
| 2005/0173245 A1 | 8/2005 | Feldman et al. | 2006/0224109 A1 | 10/2006 | Steil et al. |
| 2005/0176136 A1 | 8/2005 | Burd et al. | 2006/0224141 A1 | 10/2006 | Rush et al. |
| 2005/0177036 A1 | 8/2005 | Shults et al. | 2006/0226985 A1 | 10/2006 | Goodnow et al. |
| 2005/0177398 A1 | 8/2005 | Watanabe et al. | 2006/0229512 A1 | 10/2006 | Petisce et al. |
| 2005/0181012 A1 | 8/2005 | Saint et al. | 2006/0247508 A1 | 11/2006 | Fennell |
| 2005/0182306 A1 | 8/2005 | Sloan | 2006/0247985 A1 | 11/2006 | Liamos et al. |
| 2005/0182451 A1 | 8/2005 | Griffin et al. | 2006/0258918 A1 | 11/2006 | Burd et al. |
| 2005/0187720 A1 | 8/2005 | Goode, Jr. et al. | 2006/0258929 A1 | 11/2006 | Goode, Jr. et al. |
| 2005/0192494 A1 | 9/2005 | Ginsberg | 2006/0263763 A1 | 11/2006 | Simpson et al. |
| 2005/0192557 A1 | 9/2005 | Brauker et al. | 2006/0272652 A1 | 12/2006 | Stocker et al. |
| 2005/0195930 A1 | 9/2005 | Spital et al. | 2006/0290496 A1 | 12/2006 | Peeters et al. |
| 2005/0199494 A1 | 9/2005 | Say et al. | 2007/0016381 A1 | 1/2007 | Kamath et al. |
| 2005/0203360 A1 | 9/2005 | Brauker et al. | 2007/0027381 A1 | 2/2007 | Stafford |
| 2005/0203707 A1 | 9/2005 | Tsutsui et al. | 2007/0033074 A1 | 2/2007 | Nitzan et al. |
| 2005/0214892 A1 | 9/2005 | Kovatchev et al. | 2007/0060814 A1 | 3/2007 | Stafford |
| 2005/0215871 A1 | 9/2005 | Feldman et al. | 2007/0066873 A1 | 3/2007 | Kamath et al. |
| 2005/0215872 A1 | 9/2005 | Berner et al. | 2007/0071681 A1 | 3/2007 | Gadkar et al. |
| 2005/0239154 A1 | 10/2005 | Feldman et al. | 2007/0073129 A1 | 3/2007 | Shah et al. |
| 2005/0239156 A1 | 10/2005 | Drucker et al. | 2007/0078320 A1 | 4/2007 | Stafford |
| 2005/0241957 A1 | 11/2005 | Mao et al. | 2007/0078321 A1 | 4/2007 | Mazza et al. |
| 2005/0245795 A1 | 11/2005 | Goode, Jr. et al. | 2007/0078322 A1 | 4/2007 | Stafford |
| 2005/0245799 A1 | 11/2005 | Brauker et al. | 2007/0078323 A1 | 4/2007 | Reggiardo et al. |
| 2005/0245839 A1 | 11/2005 | Stivoric et al. | 2007/0106135 A1 | 5/2007 | Sloan et al. |
| 2005/0245904 A1 | 11/2005 | Estes et al. | 2007/0124002 A1 | 5/2007 | Estes et al. |
| 2005/0251033 A1 | 11/2005 | Scarantino et al. | 2007/0149873 A1 | 6/2007 | Say et al. |
| 2005/0251083 A1 | 11/2005 | Carr-Brendel et al. | 2007/0149874 A1 | 6/2007 | Say et al. |
| 2005/0261660 A1 | 11/2005 | Choi | 2007/0149875 A1 | 6/2007 | Ouyang et al. |
| 2005/0267780 A1 | 12/2005 | Ray et al. | 2007/0151869 A1 | 7/2007 | Heller et al. |
| 2005/0271546 A1 | 12/2005 | Gerber et al. | 2007/0161879 A1 | 7/2007 | Say et al. |
| 2005/0271547 A1 | 12/2005 | Gerber et al. | 2007/0161880 A1 | 7/2007 | Say et al. |
| 2005/0272640 A1 | 12/2005 | Doyle, III et al. | 2007/0163880 A1 | 7/2007 | Woo et al. |
| 2005/0272985 A1 | 12/2005 | Kotulla et al. | 2007/0168224 A1 | 7/2007 | Letzt et al. |
| 2005/0277164 A1 | 12/2005 | Drucker et al. | 2007/0173706 A1 | 7/2007 | Neinast et al. |
| 2005/0287620 A1 | 12/2005 | Heller et al. | 2007/0173761 A1 | 7/2007 | Kanderian et al. |
| 2006/0001538 A1 | 1/2006 | Kraft et al. | 2007/0179349 A1 | 8/2007 | Hoyme et al. |
| 2006/0001550 A1 | 1/2006 | Mann et al. | 2007/0179352 A1 | 8/2007 | Randlov et al. |
| 2006/0001551 A1 | 1/2006 | Kraft et al. | 2007/0179370 A1 | 8/2007 | Say et al. |
| 2006/0003398 A1 | 1/2006 | Heller et al. | 2007/0179372 A1 | 8/2007 | Say et al. |
| 2006/0004270 A1 | 1/2006 | Bedard et al. | 2007/0191699 A1 | 8/2007 | Say et al. |
| 2006/0004271 A1 | 1/2006 | Peyser et al. | 2007/0191700 A1 | 8/2007 | Say et al. |
| 2006/0007017 A1 | 1/2006 | Mann et al. | 2007/0191702 A1 | 8/2007 | Yodfat et al. |
| 2006/0015020 A1 | 1/2006 | Neale et al. | 2007/0203407 A1 | 8/2007 | Hoss et al. |
| 2006/0015024 A1 | 1/2006 | Brister et al. | 2007/0203408 A1 | 8/2007 | Say et al. |
| 2006/0016700 A1 | 1/2006 | Brister et al. | 2007/0203410 A1 | 8/2007 | Say et al. |
| 2006/0019327 A1 | 1/2006 | Brister et al. | 2007/0203411 A1 | 8/2007 | Say et al. |
| 2006/0020186 A1 | 1/2006 | Brister et al. | 2007/0203966 A1 | 8/2007 | Brauker et al. |
| 2006/0020187 A1 | 1/2006 | Brister et al. | 2007/0208247 A1 | 9/2007 | Say et al. |
| 2006/0020188 A1 | 1/2006 | Kamath et al. | 2007/0213610 A1 | 9/2007 | Say et al. |
| 2006/0020189 A1 | 1/2006 | Brister et al. | 2007/0213657 A1 | 9/2007 | Jennewine et al. |
| 2006/0020190 A1 | 1/2006 | Kamath et al. | 2007/0215491 A1 | 9/2007 | Heller et al. |
| 2006/0020191 A1 | 1/2006 | Brister et al. | 2007/0218097 A1 | 9/2007 | Heller et al. |
| 2006/0020192 A1 | 1/2006 | Brister et al. | 2007/0232877 A1 | 10/2007 | He |
| 2006/0025663 A1 | 2/2006 | Talbot et al. | 2007/0235331 A1 | 10/2007 | Simpson et al. |
| 2006/0029177 A1 | 2/2006 | Cranford, Jr. et al. | 2007/0244380 A1 | 10/2007 | Say et al. |
| 2006/0031094 A1 | 2/2006 | Cohen et al. | 2007/0249919 A1 | 10/2007 | Say et al. |
| 2006/0036139 A1 | 2/2006 | Brister et al. | 2007/0249920 A1 | 10/2007 | Say et al. |
| 2006/0036140 A1 | 2/2006 | Brister et al. | 2007/0249922 A1 | 10/2007 | Peyser et al. |
| 2006/0036141 A1 | 2/2006 | Kamath et al. | 2007/0299617 A1 | 12/2007 | Willis |
| 2006/0036142 A1 | 2/2006 | Brister et al. | 2008/0004515 A1 | 1/2008 | Jennewine et al. |
| 2006/0036143 A1 | 2/2006 | Brister et al. | 2008/0004601 A1 | 1/2008 | Jennewine et al. |
| 2006/0036144 A1 | 2/2006 | Brister et al. | 2008/0009692 A1 | 1/2008 | Stafford |
| 2006/0036145 A1 | 2/2006 | Brister et al. | 2008/0017522 A1 | 1/2008 | Heller et al. |
| 2006/0036187 A1 | 2/2006 | Vos et al. | 2008/0021666 A1 | 1/2008 | Goode, Jr. et al. |
| 2006/0040402 A1 | 2/2006 | Brauker et al. | 2008/0029391 A1 | 2/2008 | Mao et al. |

| | | |
|---|---|---|
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0154513 A1 | 6/2008 | Kovatchev et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0278331 A1 | 11/2008 | Hayter et al. |
| 2008/0278332 A1 | 11/2008 | Fennell et al. |
| 2008/0278333 A1 | 11/2008 | Fennell et al. |
| 2008/0281171 A1 | 11/2008 | Fennell et al. |
| 2008/0281179 A1 | 11/2008 | Fennell et al. |
| 2008/0281840 A1 | 11/2008 | Fennell et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300919 A1 | 12/2008 | Charlton et al. |
| 2008/0300920 A1 | 12/2008 | Brown et al. |
| 2008/0301158 A1 | 12/2008 | Brown et al. |
| 2008/0301665 A1 | 12/2008 | Charlton et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0105636 A1 | 4/2009 | Hayter et al. |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0143660 A1 | 6/2009 | Brister et al. |
| 2009/0149717 A1 | 6/2009 | Brauer et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0318789 A1 | 12/2009 | Fennell et al. |
| 2009/0318792 A1 | 12/2009 | Fennell et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |

| | | | | | | |
|---|---|---|---|---|---|---|
| 2010/0036215 | A1 | 2/2010 | Goode, Jr. et al. | JP | 55-010581 | 1/1980 |
| 2010/0036216 | A1 | 2/2010 | Goode, Jr. et al. | JP | 55-010583 | 1/1980 |
| 2010/0036222 | A1 | 2/2010 | Goode, Jr. et al. | JP | 55-010584 | 1/1980 |
| 2010/0036223 | A1 | 2/2010 | Goode, Jr. et al. | JP | 55-012406 | 1/1980 |
| 2010/0036225 | A1 | 2/2010 | Goode, Jr. et al. | JP | 56-163447 | 12/1981 |
| 2010/0041971 | A1 | 2/2010 | Goode, Jr. et al. | JP | 57-070448 | 4/1982 |
| 2010/0045465 | A1 | 2/2010 | Brauker et al. | JP | 60-173457 | 9/1985 |
| 2010/0049024 | A1 | 2/2010 | Saint et al. | JP | 60-173458 | 9/1985 |
| 2010/0057040 | A1 | 3/2010 | Hayter | JP | 60-173459 | 9/1985 |
| 2010/0057041 | A1 | 3/2010 | Hayter | JP | 60-210243 | 10/1985 |
| 2010/0057042 | A1 | 3/2010 | Hayter | JP | 61-090050 | 5/1986 |
| 2010/0057044 | A1 | 3/2010 | Hayter | JP | 62-085855 | 4/1987 |
| 2010/0057057 | A1 | 3/2010 | Hayter et al. | JP | 62-114747 | 5/1987 |
| 2010/0063373 | A1 | 3/2010 | Kamath et al. | JP | 63-058149 | 3/1988 |
| 2010/0076283 | A1 | 3/2010 | Simpson et al. | JP | 63-128252 | 5/1988 |
| 2010/0081908 | A1 | 4/2010 | Dobbles et al. | JP | 63-139246 | 6/1988 |
| 2010/0081910 | A1 | 4/2010 | Brister et al. | JP | 63-294799 | 12/1988 |
| 2010/0087724 | A1 | 4/2010 | Brauker et al. | JP | 63-317757 | 12/1988 |
| 2010/0096259 | A1 | 4/2010 | Zhang et al. | JP | 63-317758 | 12/1988 |
| 2010/0099970 | A1 | 4/2010 | Shults et al. | JP | 1-114746 | 5/1989 |
| 2010/0099971 | A1 | 4/2010 | Shults et al. | JP | 1-114747 | 5/1989 |
| 2010/0119693 | A1 | 5/2010 | Tapsak et al. | JP | 1-124060 | 5/1989 |
| 2010/0121169 | A1 | 5/2010 | Petisce et al. | JP | 1-134244 | 5/1989 |

FOREIGN PATENT DOCUMENTS

| | | |
|---|---|---|
| JP | 1-156658 | 6/1989 |
| DE | 227029 | 9/1985 |
| JP | 2-062958 | 3/1990 |
| DE | 3934299 | 10/1990 |
| JP | 2-120655 | 5/1990 |
| DE | 4234553 | 1/1995 |
| JP | 2-287145 | 11/1990 |
| DE | 4401400 | 7/1995 |
| JP | 2-310457 | 12/1990 |
| EP | 0010375 | 4/1980 |
| JP | 3-026956 | 2/1991 |
| EP | 1579690 | 11/1980 |
| JP | 3-028752 | 2/1991 |
| EP | 0026995 | 4/1981 |
| JP | 3-202764 | 9/1991 |
| EP | 0048090 | 3/1982 |
| JP | 5-072171 | 3/1993 |
| EP | 0078636 | 5/1983 |
| JP | 5-196595 | 8/1993 |
| EP | 0080304 | 6/1983 |
| JP | 6-190050 | 7/1994 |
| EP | 0096228 | 12/1983 |
| JP | 7-055757 | 3/1995 |
| EP | 0096288 | 12/1983 |
| JP | 7-072585 | 3/1995 |
| EP | 0098592 | 1/1984 |
| JP | 8-154903 | 6/1996 |
| EP | 0125139 | 11/1984 |
| JP | 8-285814 | 11/1996 |
| EP | 0127958 | 12/1984 |
| JP | 8-285815 | 11/1996 |
| EP | 0136362 | 4/1985 |
| JP | 9-021778 | 1/1997 |
| EP | 0170375 | 2/1986 |
| JP | 9-101280 | 4/1997 |
| EP | 0177743 | 4/1986 |
| JP | 9-285459 | 11/1997 |
| EP | 0184909 | 6/1986 |
| JP | 10-170471 | 6/1998 |
| EP | 0206218 | 12/1986 |
| JP | 2000-000231 | 1/2000 |
| EP | 0230472 | 8/1987 |
| JP | 2000-116628 | 4/2000 |
| EP | 0241309 | 10/1987 |
| SU | 1281988 | 1/1987 |
| EP | 0245073 | 11/1987 |
| WO | WO-85/05119 | 11/1985 |
| EP | 0255291 | 2/1988 |
| WO | WO-86/00513 | 1/1986 |
| EP | 0278647 | 8/1988 |
| WO | WO-87/00513 | 1/1987 |
| EP | 0320109 | 6/1989 |
| WO | WO-87/06040 | 10/1987 |
| EP | 0353328 | 2/1990 |
| WO | WO-89/02246 | 3/1989 |
| EP | 0359831 | 3/1990 |
| WO | WO-89/05119 | 6/1989 |
| EP | 0368209 | 5/1990 |
| WO | WO-89/08713 | 9/1989 |
| EP | 0368290 | 5/1990 |
| WO | WO-90/00367 | 1/1990 |
| EP | 0390390 | 10/1990 |
| WO | WO-90/05300 | 5/1990 |
| EP | 0396788 | 11/1990 |
| WO | WO-90/05910 | 5/1990 |
| EP | 0400918 | 12/1990 |
| WO | WO-91/01680 | 2/1991 |
| EP | 0453283 | 10/1991 |
| WO | WO-91/04704 | 4/1991 |
| EP | 0470290 | 2/1992 |
| WO | WO-91/15993 | 10/1991 |
| EP | 0504835 | 9/1992 |
| WO | WO-92/01947 | 2/1992 |
| EP | 0286118 | 1/1995 |
| WO | WO-92/13271 | 8/1992 |
| EP | 0653718 | 5/1995 |
| WO | WO-94/20602 | 9/1994 |
| EP | 0800082 | 10/1997 |
| WO | WO-94/27140 | 11/1994 |
| EP | 0880936 | 12/1998 |
| WO | WO-95/06240 | 3/1995 |
| EP | 0970655 | 1/2000 |
| WO | WO-96/07908 | 3/1996 |
| EP | 1034734 | 9/2000 |
| WO | WO-96/25089 | 8/1996 |
| EP | 1048264 | 11/2000 |
| WO | WO-96/30431 | 10/1996 |
| EP | 1445746 | 8/2004 |
| WO | WO-96/35370 | 11/1996 |
| GB | 1394171 | 5/1975 |
| WO | WO-97/02847 | 1/1997 |
| GB | 1579690 | 11/1980 |
| WO | WO-97/19344 | 5/1997 |
| GB | 1599241 | 9/1981 |
| WO | WO-97/20207 | 6/1997 |
| GB | 2073891 | 10/1981 |
| WO | WO-97/41421 | 11/1997 |
| GB | 2154003 | 8/1985 |
| WO | WO-97/42882 | 11/1997 |
| GB | 2194892 | 3/1988 |
| WO | WO-97/42883 | 11/1997 |
| GB | 2204408 | 11/1988 |
| WO | WO-97/42886 | 11/1997 |
| GB | 2225637 | 6/1990 |
| WO | WO-97/42888 | 11/1997 |
| GB | 2254436 | 10/1992 |
| WO | WO-97/43962 | 11/1997 |
| JP | 54-041191 | 4/1979 |
| WO | WO-97/46868 | 12/1997 |
| | | |
| | | WO | WO-98/09167 | 3/1998 |

| | | |
|---|---|---|
| WO | WO-98/24366 | 6/1998 |
| WO | WO-98/35053 | 8/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/56613 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/67009 | 9/2001 |
| WO | WO-02/13686 | 2/2002 |
| WO | WO-02/16905 | 2/2002 |
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2006/024671 | 3/2006 |
| WO | WO-2006/037109 | 4/2006 |
| WO | WO-2006/079114 | 7/2006 |
| WO | WO-2006/118947 | 11/2006 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/053832 | 5/2007 |
| WO | WO-2007/056638 | 5/2007 |
| WO | WO-2007/101223 | 9/2007 |
| WO | WO-2007/101260 | 9/2007 |
| WO | WO-2007/120363 | 10/2007 |
| WO | WO-2007/126444 | 11/2007 |
| WO | WO-2007/143225 | 12/2007 |
| WO | WO-2008/003003 | 1/2008 |
| WO | WO-2008/005780 | 1/2008 |
| WO | WO-2008/021913 | 2/2008 |
| WO | WO-2008/042760 | 4/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/150428 | 12/2008 |
| WO | WO-2008/153825 | 12/2008 |
| WO | WO-2009/018058 | 2/2009 |
| WO | WO-2009/075697 | 6/2009 |
| WO | WO-2009/086216 | 7/2009 |
| WO | WO-2009/096992 | 8/2009 |
| WO | WO-2009/097594 | 8/2009 |

OTHER PUBLICATIONS

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", Web Page of Boedeker.com, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/88, pp. 45-56.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion As An Electron Acceptor for Oxido-Reductases", *Journal of ElectroAnalytical Chemistry*, vol. 190, 1985, pp. 117-127.

Cass, A. E., et al., "Ferrocene-Mediated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous In Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Complaint, "*Abbott Diabetes Care, Inc.* v. *Dexcom, Inc.*", filed Aug. 11, 2005.
Complaint, Amended, "*Abbott Diabetes Care, Inc.* v. *Dexcom, Inc.*", filed Jun. 27, 2006.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.
Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.
Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.
Davis, G., "Electrochemical Techniques for the Development of Amperometric Biosensors", *Biosensors*, vol. 1, 1985, pp. 161-178.
DeGani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.
Degani, Y., et al., "Electrical Communication Between Redox Centers of Glucose Oxidase Electrodes via Electrostatically and Covalently Bound Redox Polymers", *Journal of the American Chemical Society*, vol. 111, 1989, pp. 2357-2358.
Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.
Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.
Ellis, C. D., et al., "Selectivity and Directed Charge Transfer through an Electroactive Metallopolymer Film", *Journal of the American Chemical Society*, vol. 103, No. 25, 1981, pp. 7480-7483.
Engstrom, R. C., "Electrochemical Pretreatment of Glassy Carbon Electrodes", *Analytical Chemistry*, vol. 54, No. 13, 1982, pp. 2310-2314.
Engstrom, R. C., et al., "Characterization of Electrochemically Pretreated Glassy Carbon Electrodes", *Analytical Chemistry*, vol. 56, No. 2, 1984, pp. 136-141.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*.
Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.
Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.
Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.
Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.
Foulds, N. C., et al, "Immobilization of Glucose Oxidase in Ferrocene-Modified Pyrrole Polymers", *Analytical Chemistry*, vol. 60, No. 22, 1988, pp. 2473-2478.
Frew, J. E., et al., "Electron-Transfer Biosensors", *Philosophical Transactions of The Royal Society of London*, vol. 316, 1987, pp. 95-106.
Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.
Gorton, L., et al., "Selective Detection in Flow Analysis Based on the Combination of Immobilized Enzymes and Chemically Modified Electrodes", *Analytica Chimica Acta*, vol. 250, 1991, pp. 203-248.
Graham, N. B., "Poly(ethylene oxide) and Related Hydrogels," *Hydrogels in Medicine and Pharmacy*, vol. II: Polymers, Chapter 4, 1987, pp. 95-113.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.
Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.
Hamilton, "Hamilton Needle Gauge Index", www.hamiltoncompany.com.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Hawkridge, F. M., et al., "Indirect Coulometric Titration of Biological Electron Transport Components", *Analytical Chemistry*, vol. 45, No. 7, 1973, pp. 1021-1027.
Heller, A., "Electrical Connection Enzyme Redox Centers to Electrodes", *Journal of Physical Chemistry*, vol. 96, No. 9, 1990, pp. 3579-3587.
Heller, A., "Electrical Wiring of Redox Enzymes", *Accounts of Chemical Research* vol. 23, No. 5, 1990, 128-134.
Heller, A., et al., "Amperometric Biosensors Based on Three-Dimensional Hydrogel-Forming Epoxy Networks", *Sensors and Actuators B*, vol. 13-14, 1993, pp. 180-183.
Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.
Ianniello, R. M., et al , "Immobilized Enzyme Chemically Modified Electrode as an Amperometric Sensor", *Analytical Chemistry*, vol. 53, No. 13, 1981, pp. 2090-2095.
Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.
Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, J. M., et al., "Potential-Dependent Enzymatic Activity in an Enzyme Thin-Layer Cell", *Analytical Chemistry*, vol. 54, No. 8, 1982, pp. 1377-1383.
Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2Cl]^{+/2+}$", *Journal of the Chemical Society, Faraday Transactions*, vol. 92 No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", *TheraSense, Inc.*, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for In Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and In Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds,"*Virtual Textbook of Organic Chemistry*, 1999, Rev. 2007, 25 pages.

Roe, J. N., et al., "Bloodless Glucose Measurements", *Critical Review in Therapeutic Drug Carrier Systems*, vol. 15, Issue 3, 1998, pp. 199-241.

Sacks (ED), "Guidelines and Recommendations for Laboratory Analysis in the Diagnosis Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV) pH 'Encapsulation' in a Polymer Film", *Journal of the American Chemical Society*, vol. 103, No. 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors,"*Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of of Analytical Data," *Fundamentals Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M , "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer- and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Travenol Laboratories, Inc., *An Introduction to "Eugly"*, Book 1, 1985, pp. 1-22.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

U.S. Patent Reexamination Application No. 90/007,903, Request for Reexamination of U.S. Patent No. 6,565,509, filed Jan. 25, 2006.

U.S. Patent Reexamination Application No. 90/007,910, Request for Reexamination of U.S. Patent No. 6,175,752, filed Feb. 1, 2006.

U.S. Patent Reexamination Application No. 90/007,913, Request for Reexamination of U.S. Patent No. 6,284,478, filed Feb. 1, 2006.

U.S. Patent Reexamination Application No. 90/007,914, Request for Reexamination of U.S. Patent No. 6,329,161, filed Feb. 1, 2006.

U.S. Patent Reexamination Application No. 90/008,172, Request for Reexamination of U.S. Patent No. 6,990,366, filed Aug. 16, 2006.

U.S. Patent Reexamination Application No. 90/008,173, Request for Reexamination of U.S. Patent No. 6,134,461, filed Aug. 16, 2006.

U.S. Patent Reexamination Application No. 90/008,457, Request for Reexamination of U.S. Patent No. 6,990,366, filed Jan. 23, 2007.

U.S. Patent Reexamination Application No. 90/008,665, Request for Reexamination of U.S. Patent No. 6,284,478, filed May 25, 2007.

U.S. Patent Reexamination Application No. 90/008,713, Request for Reexamination of U.S. Patent No. 6,329,161, filed Jul. 25, 2007.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and In Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

\* cited by examiner

ANALYTE MONITORING DEVICES AND METHODS THEREFOR

BACKGROUND OF THE INVENTION

In diabetes management, there exist devices which allow diabetic patients to measure the blood glucose levels. One such device is a hand-held electronic meter such as blood glucose meters such as Freestyle® blood glucose monitoring system available from Abbott Diabetes Care, Inc., of Alameda, Calif. which receives blood samples via enzyme-based test strips. Typically, the patient lances a finger or alternate body site to obtain a blood sample, applies the drawn blood sample to the test strip, and the strip is inserted into a test strip opening or port in the meter housing. The blood glucose meter converts a current generated by the enzymatic reaction in the test strip to a corresponding blood glucose value which is displayed or otherwise provided to the patient to show the level of glucose at the time of testing.

Such periodic discrete glucose testing helps diabetic patients to take any necessary corrective actions to better manage diabetic conditions. Presently available glucose meters have limited functionalities (for example, providing the glucose value measured using the test strip and storing the data for subsequent recall or display) and do not provide any additional information or capability to assist patients in managing diabetes. For example, Type-1 diabetic patients who require periodic infusion or injection of insulin, typically use glucose meters in addition to, for example, wearing an external infusion device, or a pen type injection device. Also, in the case of external infusion devices, because of the strip port on the meter receives the test strip (which is generally not a water tight seal), it is not desirable to incorporate the discrete glucose meter functionalities to the housing of the external infusion devices.

With the decreasing cost of electronic components and a corresponding increase in data processing capabilities of microprocessors, computational capability of electronic devices have been rapidly increasing. However, currently available glucose meters are generally configured with limited functionalities related to discrete glucose testing.

In view of the foregoing, it would be desirable to have a glucose meter, such as a blood glucose meter, with various functionalities. Of interest are glucose meters are capable of providing bolus dosage calculation, and the like, and which incorporate additional features related to diabetes management.

SUMMARY OF THE INVENTION

In view of the foregoing, in accordance with the various embodiments of the present invention, there are provided methods and system for incorporating the bolus calculation function into a blood glucose meter device which may be configured to perform data analysis and management based on, for example, the glucose level detected using the glucose meter.

These and other objects, features and advantages of the present invention will become more fully apparent from the following detailed description of the embodiments, the appended claims and the accompanying drawings.

DETAILED DESCRIPTION

As described in further detail below, in accordance with the various embodiments of the present invention, there are provided blood glucose meter devices that include bolus calculation functions and related data analysis capabilities incorporated in the glucose meter devices.

Figure 1:
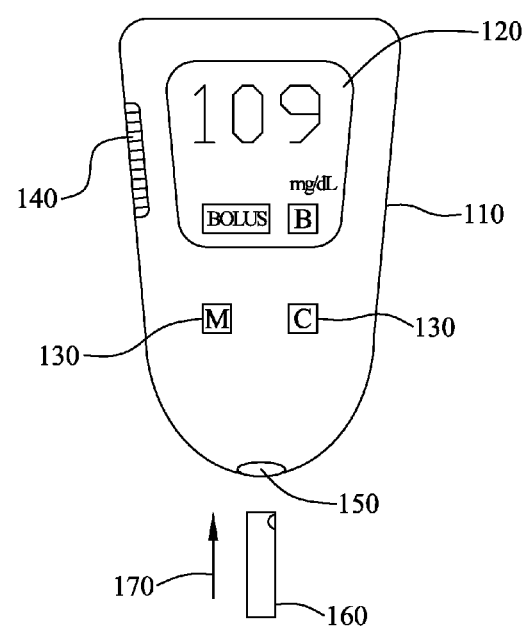
FIG. 1 is a glucose meter with bolus calculation function in accordance with one embodiment of the present invention.

FIG. 1 shows a glucose meter with bolus calculation function in accordance with one embodiment of the present invention. Glucose meter with bolus calculation function 100 includes a housing 110 with a display unit 120 provided thereon. Also shown in FIG. 1 is a plurality of input buttons 130, each configured to allow the user of the glucose meter with bolus calculation function 100 to input or enter data or relevant information associated with the operation of the glucose meter with bolus calculation function 100. For example, the user of the glucose meter with bolus calculation function may operate the one or more input buttons 130 to enter a calibration code associated with a test strip 160 for use in conjunction with the glucose meter with bolus calculation function 100. Additionally, the user may operate the one or more input buttons 130 to adjust time and/or date information, as well as other features or settings associated with the operation of the glucose meter with bolus calculation function 100.

Referring back to FIG. 1, also shown is input unit 140 which, in one embodiment, may be configured as a jog dial, or the like, and provided on the housing 110 of the glucose meter with bolus calculation function 100. In one embodiment, as discussed in further detail below, the user or the patient may operate the input unit 140 to perform calculations and determinations associated with one or more bolus estimation functions of the glucose meter with bolus calculation function 100. Also shown in FIG. 1 is a strip port 150 which is configured to receive the test strip 160 (with blood sample provided thereon) substantially in the direction as shown by the directional arrow 170.

In operation, when the test strip 160 with the patient's blood sample is inserted into the strip port 150 of the glucose meter with bolus calculation function 100, a micro processor or a control unit 210 (FIG. 2) of the glucose meter with bolus calculation function 100 may be configured to determine the associated glucose level in the blood sample, and display the determined glucose level on the display unit 120.

In addition, in accordance with the various embodiments of the present invention, the glucose meter with bolus calculation function 100 may be configured to automatically enter into a bolus determination mode to, for example, estimate the predetermined or preprogrammed bolus dosage amount based on information stored in the glucose meter with bolus calculation function 100 (such as the patient's insulin sensitivity, for example), and/or prompt the patient to provide additional information, such as the amount of carbohydrate to be ingested by the patient for determination of, for example, a carbohydrate bolus dosage determination. The patient may operate the input unit 140 in conjunction with the user interface menu provided on the display unit 120 to provide the appropriate information.

In another embodiment, the glucose meter with bolus calculation function 100 may be configured to prompt the patient to select whether to calculate a predetermined or preprogrammed bolus dosage amount such as, for example, a correction bolus or a carbohydrate bolus, following the display of the determined glucose level from the test strip 160. In this manner, in one embodiment of the present invention, the glucose meter with bolus calculation function 100 may be configured to automatically prompt the user or patient to select whether a bolus dosage determination is desired following a glucose testing using the test strip 160.

Figure 2:
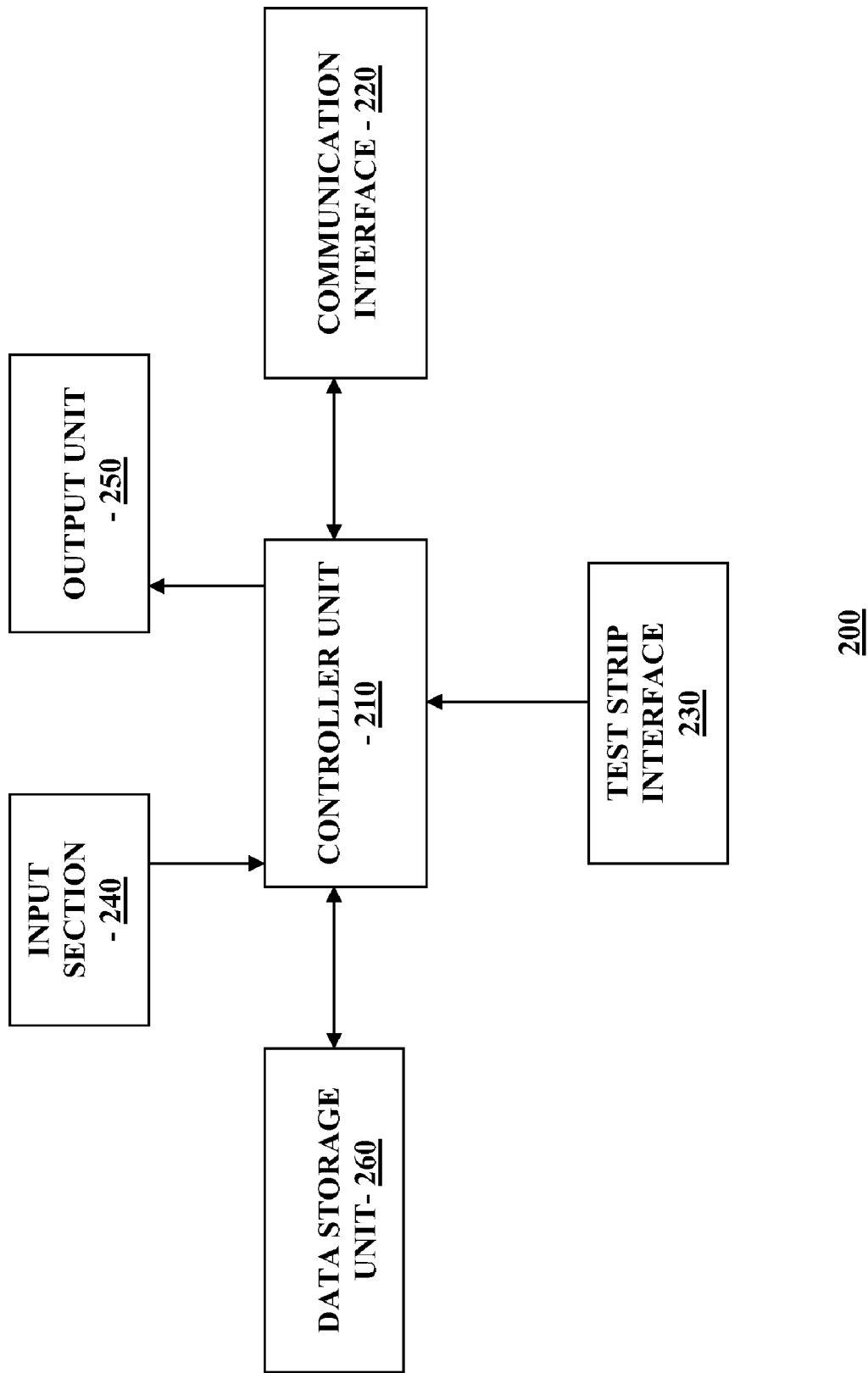
FIG. 2 is a block diagram of the glucose meter with bolus calculation function of FIG. 1 in one embodiment of the present invention.

FIG. 2 is a block diagram of the glucose meter with bolus calculation function of FIG. 1 in one embodiment of the present invention. Referring to FIG. 2, the glucose meter with bolus calculation function 200 includes a controller unit 210 operatively coupled to a communication interface 220 and configured for bidirectional communication. The controller unit 210 is further operatively coupled to a test strip interface 230, an input section 240 (which, for example, may include the input unit 140 and the plurality of input buttons 130 as shown in FIG. 1), an output unit 250, and a data storage unit 260.

Referring to FIG. 2, in one embodiment of the present invention, the test strip interface 230 is configured to couple with the inserted test strip 160 for determination of the blood sample on the test strip 160. In addition, the test strip interface 230 may include an illumination segment which may be configured to illuminate the strip port 150 (FIG. 1) using a light emitting diode (LED), for example, during the test strip 160 insertion process to assist the user in properly and accurately inserting the test strip 160 into the strip port 150.

Moreover, in a further aspect of the present invention, the test strip interface 230 may be additionally configured with a physical latch or securement mechanism internally provided within the housing 110 of the glucose meter with bolus calculation function 100 (FIG. 1) such that when the test strip 160 is inserted into the strip port 150, the test strip 160 is retained in the received position within the strip port 150 until the sample analysis is completed. Examples of such physical latch or securement mechanism may include a uni-directionally biased anchor mechanism, or a pressure application mechanism to retain the test strip 160 in place by applying pressure on one or more surfaces of the test strip 160 within the strip port 150.

Referring back to FIG. 1, the output unit 250 may be configured to output display data or information including the determined glucose level on the display unit 120 (FIG. 1) of the glucose meter with bolus calculation function 100. In addition, in still a further aspect of the present invention, the output unit 250 and the input section 240 may be integrated, for example, in the case where the display unit 120 is configured as a touch sensitive display where the patient may enter information or commands via the display area using, for example, a stylus or any other suitable input device, and where, the touch sensitive display is configured as the user interface in an icon driven environment, for example.

Referring yet again to FIG. 2, the communication interface 220 in one embodiment of the present invention includes a wireless communication section configured for bi-directional radio frequency (RF) communication with other devices to transmit and/or receive data to and from the glucose meter with bolus calculation function 100. In addition, the communication interface 220 may also be configured to include physical ports or interfaces such as a USB port, an RS-232 port, or any other suitable electrical connection port to allow data communication between the glucose meter with bolus calculation function 100 and other external devices such as a computer terminal (for example, at a physician's office or in hospital environment), an external infusion device such as insulin pumps, or other devices that is configured for similar complementary data communication.

In one embodiment, the wireless communication section of the communication interface 220 may be configured for infrared communication, Bluetooth communication, or any other suitable wireless communication mechanism to enable the glucose meter with bolus calculation function to communication with other devices such as infusion devices, analyte monitoring devices, computer terminals, communication enabled mobile telephones, personal digital assistants, or any other communication devices which the patient or user of the glucose meter with bolus calculation function 100 may use in conjunction therewith, in managing the treatment of the diabetic condition.

Figure 3:
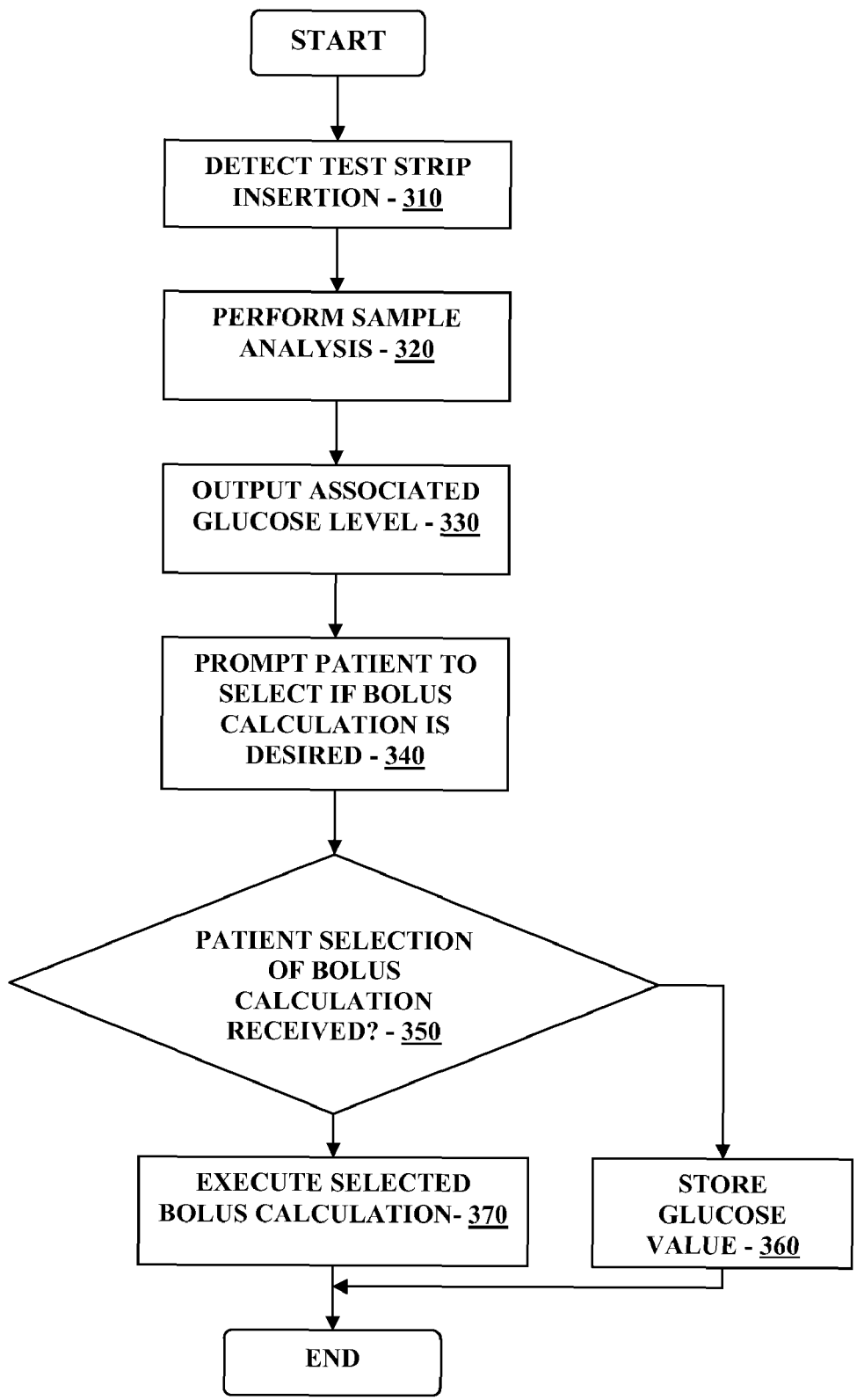
FIG. 3 is a flowchart illustrating the glucose level determination and bolus calculation procedure in accordance with one embodiment of the present invention.

FIG. 3 is a flowchart illustrating the glucose level determination and bolus calculation procedure in accordance with one embodiment of the present invention. Referring to FIG. 3, a test strip is detected by the controller unit 210 (or the test strip interface 230) 310 of the glucose meter with bolus calculation function 100 (FIG. 1). Thereafter, the blood sample received from the inserted test strip 150 is analyzed 320 to determine the corresponding glucose level, and the determined glucose level is output 330 on the display unit 120 (FIG. 1) for example, in units of mg/dL.

Referring back to FIG. 3, after determining the glucose level and displaying the measured glucose level to the patient 330, a prompt command is generated and output to the patient to select if the bolus calculation is desired 340. More specifically, in one embodiment of the present invention, the controller unit 210 is configured to generate a command and display in the display unit 120 to query the user as to whether a bolus calculation determination is desired by the patient. Thereafter, a determination of whether or not the patient has selected to have the bolus dosage calculation performed by the controller unit 210 is made 350. In one embodiment, the patient may operate one or more of the input buttons 130 or the input unit 140 to select whether or not to have the bolus calculation performed.

Referring again to FIG. 3, if it is determined that the patient has selected not to have the bolus dosage determination performed, then the determined glucose value is stored 360, e.g., in memory of the meter, and the routine terminates. For example, in one embodiment, the controller unit 210 (FIG. 2) may be configured to store the determined glucose value in the data storage unit 260 with associated time and/or date information of when the glucose value determination is performed. In an alternate embodiment, the measured glucose value may be stored substantially concurrently with the display of the glucose value (for example, 330).

On the other hand, if it is determined that the patient has selected to have the bolus dosage calculation performed, the glucose meter with bolus calculation function 100 is configured to enter the bolus dosage determination mode 370, described in further detail below in conjunction with FIG. 4, where the desired type of bolus dosage is determined and provided to the patient.

Figure 4:
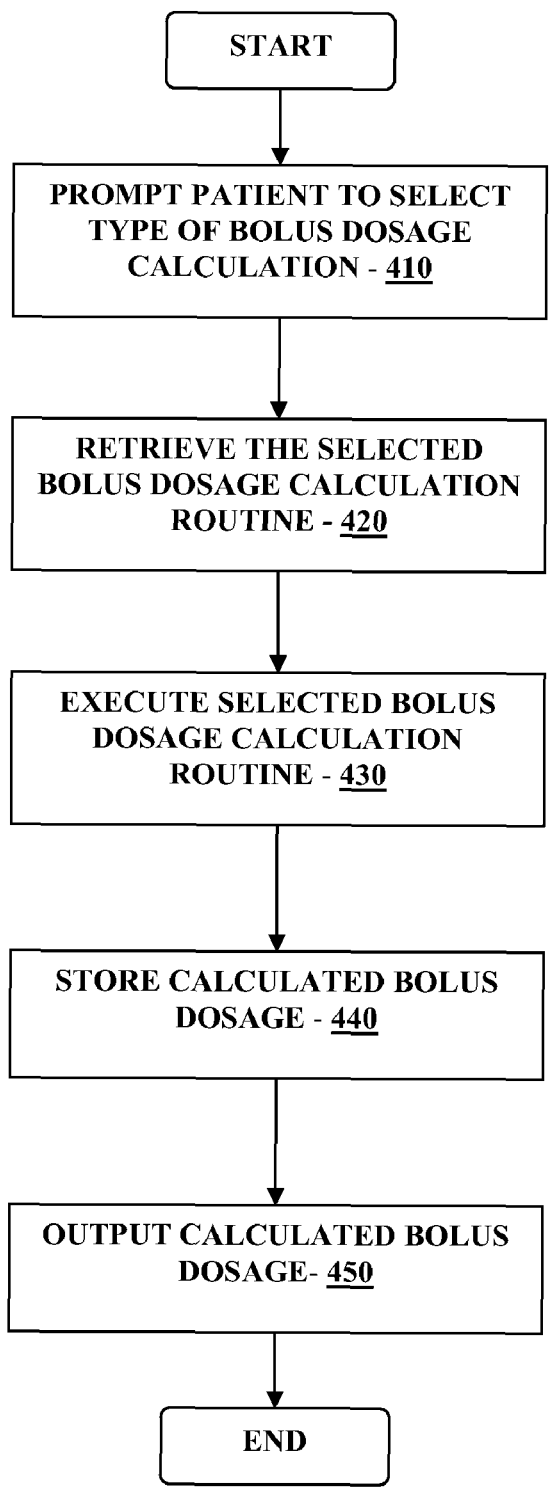
FIG. 4 is a flowchart illustrating the bolus calculation procedure of FIG. 3 in accordance with one embodiment of the present invention.

FIG. 4 is a flowchart illustrating the bolus calculation procedure of FIG. 3 in accordance with one embodiment of the present invention. Referring to FIG. 4, when the glucose meter with bolus calculation function 100 (FIG. 1) enters the bolus dosage determination mode as described above, the controller unit 210 (FIG. 2) is configured to prompt the patient (for example, by displaying the options to the patient on the display unit 120 (FIG. 1)) to select the type of desired bolus dosage calculation 410. For example, the controller unit 210 may be configured to output a list of available bolus dosage calculation options including, for example, a carbohydrate bolus, a correction bolus, a dual or extended bolus, a square wave bolus, or any other suitable bolus calculation function which may be programmed into the glucose meter with bolus calculation function 100 (and for example, stored in the data storage unit 260).

Referring back to FIG. 4, after the patient selects the desired bolus dosage calculation in response to the prompt for bolus type selection 410, the selected bolus dosage calculation routine is retrieved 420 from the data storage unit 260, thereafter executed 430. In one embodiment, the execution of the selected bolus dosage calculation 430 may include one or more input prompts to the patient to enter additional information as maybe required to perform the selected bolus dosage calculation.

For example, in the case of calculating a carbohydrate bolus, the patient may be prompted to provide or enter an estimate of the carbohydrate amount that the patient is planning on ingesting 430. In this regard, a food database may be stored in the data storage unit 260 or elsewhere for easy access (e.g., a PC, PDA, telephone, or the like and to which the meter may be coupled (e.g., wirelessly or by physical connection) to easily retrieve such information) to conveniently determine the corresponding carbohydrate amount associated with the type of food which the patient will be ingesting. Alternatively, the patient may provide the actual estimated carbohydrate count if such information is readily available by the patient.

Alternatively, in the case of calculating a dual bolus, the patient is prompted to provide a time duration information for the extended portion of the bolus dosage to be infused or otherwise provided to the patient. Similarly, the patient may further be prompted to provide insulin sensitivity information, and any other information as maybe necessary to determine the selected bolus dosage amount in conjunction with other relevant information such as insulin on board information, and the time of the most recently administered bolus (so as to provide a warning to the patient if a bolus dosage has been administered within a predetermined time period, and a subsequent administration of the additional bolus dosage may potentially be harmful).

Referring back to FIG. 4, after the execution of the selected bolus dosage calculation routine 430, the calculated bolus dosage amount is stored 440 in the data storage unit 260, and the calculated bolus dosage amount is output displayed to the patient 450 on the display unit 120 of the glucose meter with bolus calculation function 100, or audibly if the meter is so configured. In certain embodiments, storing and output displaying the calculated bolus dosage amount may be substantially concurrently performed, rather than sequentially.

Figure 5:
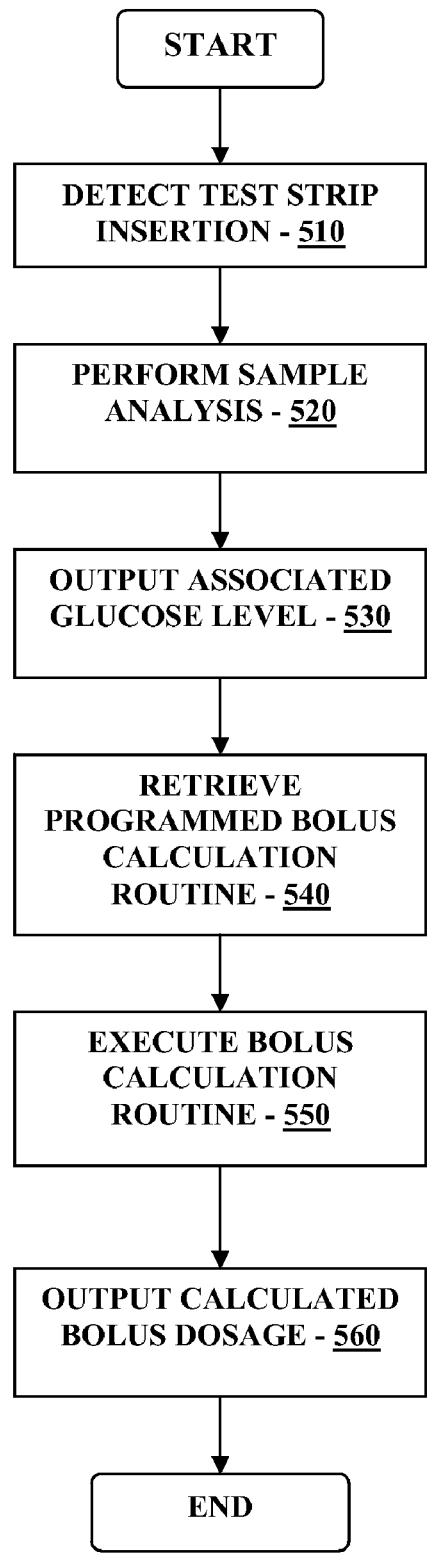
FIG. 5 is a flowchart illustrating the glucose level determination and bolus calculation procedure in accordance with another embodiment of the present invention.

FIG. 5 is a flowchart illustrating the glucose level determination and bolus calculation procedure in accordance with another embodiment of the present invention. Referring to FIG. 5, a test strip 160 is inserted into the strip port of the glucose meter with bolus calculation function 510, the blood sample on the test strip 160 is analyzed to determine the corresponding blood glucose level 520, and thereafter, output displayed 530.

Referring back to FIG. 5, a determination of the blood glucose level from the blood sample received from the test strip 160, is made 540. The controller unit 210 (FIG. 2) is configured to enter into the bolus dosage determination mode, and to execute preprogrammed or predetermined bolus calculation routine 550, and thereafter, output display the calculated bolus dosage amount 560. In this manner, in one embodiment of the present invention, the glucose meter with bolus calculation function 100 may be programmed or configured to automatically enter into the dosage determination mode upon completion of the blood sample analysis for glucose level determination.

In one embodiment of the present invention, the glucose meter with bolus calculation function 100 may be configured to execute different types of bolus dosage calculation based on the patient specified parameters. For example, the glucose meter with bolus calculation function 100 may be configured to perform a carbohydrate bolus determination when the test strip sample analysis is performed within a predetermined time period of a meal event. For example, the glucose meter with bolus calculation function 100 may be programmed by the patient to automatically select the carbohydrate bolus determination if the test strip blood sample analysis is performed within one hour prior to a meal time (which may be programmed into the glucose meter with bolus calculation function 100).

Accordingly, as described herein, embodiments of the present invention, method and apparatus for performing discrete glucose testing and bolus dosage determination are provided.

An apparatus including a glucose meter in one embodiment of the present invention includes a housing having a display unit disposed thereon, a strip port coupled to the housing and a controller unit coupled to the housing, a controller configured to process one or more signals associated with data received from the test strip, and a controller (the same or different controller from the controller described above) configured to determined a bolus dosage based on the data received from the test strip.

The controller may be configured to display the determined bolus dosage on the display unit, where the displayed bolus dosage may be one or more of an alphanumeric display, a graphical display, a video display, an audio display, a vibratory output, or combinations thereof.

In a further aspect, the controller unit may be configured to determine the bolus dosage substantially automatically after receiving the data from the test strip.

In one embodiment, the apparatus may include an output unit configured to provide one or more of an audible notification, a vibratory notification, or combinations thereof.

Moreover, the bolus dosage determined by the controller unit may include one or more of a carbohydrate bolus, a correction bolus, an extended bolus, a dual bolus, or combinations thereof.

The apparatus in yet another embodiment may include an input unit coupled to the housing, where the controller unit may be configured to determine the bolus dosage in response to a command received from the input unit.

The input unit may include one or more of an input button, a touch sensitive screen, a jog wheel, or combinations thereof.

Further, the data received from the test strip may correspond to an analyte level which, in one embodiment may include a measured glucose level of a patient.

A computer program product for use with a glucose meter in accordance with a further embodiment of the present invention includes a computer readable storage medium having a computer program stored thereon which controls the meter to calculate a bolus dosage based on glucose information received from the meter.

In one aspect, the glucose meter may be configured to display the calculated bolus dosage. The bolus dosage displayed on the glucose meter may be one or more of an alphanumeric display, a graphical display, a video display, an audio display, a vibratory output, or combinations thereof.

In a further aspect, the bolus dosage may include one or more of a carbohydrate bolus, a correction bolus, an extended bolus, a dual bolus, or combinations thereof.

Also provided are methods of analyte monitoring. Embodiments include receiving an analyte sample, determining an analyte level corresponding to the analyte sample, and determining a bolus dosage amount substantially immediately after the analyte level determination.

In one embodiment, the method may include displaying one or more of the bolus dosage, the analyte level, or combinations thereof. Determining a bolus dosage in some embodiments may be automatically performed after the analyte level determination.

The method may include generating one or more of an audible notification, a vibratory notification, a visual notification, or combinations thereof, associated with one or more of the determined bolus dosage, the determined analyte level, or combinations thereof.

The bolus dosage determined in one embodiment may include one or more of a carbohydrate bolus, a correction bolus, an extended bolus, a dual bolus, or combinations thereof.

The various processes described above including the processes performed by the processor unit 210 in the software application execution environment of the glucose meter device 200 including the processes and routines described in conjunction with FIGS. 3-5, may be embodied as computer programs developed using an object oriented language that allows the modeling of complex systems with modular objects to create abstractions that are representative of real world, physical objects and their interrelationships. The software required to carry out the inventive process, which may be stored in the storage unit 260 (FIG. 2) of the glucose meter with bolus calculation function 100, may be developed by a person of ordinary skill in the art and may include one or more computer program products.

A computer program product is also provided that is configured for use with a glucose meter. The program product includes a computer readable storage medium having a computer program stored thereon for calculating a bolus based on glucose information from the meter. For example, a meter controller may include a general purpose digital microprocessor or the like that may be programmed from such a computer readable medium carrying necessary program code for accomplishing the bolus function described herein. The programming may be provided remotely to the meter controller, e.g., through a communication channel, or previously saved in a computer program product such as memory or some other portable or fixed computer readable storage medium. For example, a magnetic or optical disk may carry the programming, which may be read by a reader of the meter and optionally stored in meter memory the meter. The computer program product may be any suitable product, such as a portable or fixed computer readable storage medium, including magnetic or optical disks or tape or RAM, or any other suitable device, either fixed or portable.

Various other modifications and alternations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. An apparatus including a glucose meter, comprising:
a housing having a display unit disposed thereon;
a data storage unit disposed within the housing, the data storage unit storing meal event information;
a strip port coupled to the housing and configured to receive a test strip therein; and
a controller unit coupled to the housing, the controller configured to process one or more signals associated with data received from the test strip, and to provide an output to the display unit based on the processed one or more signals, after providing the output based on the processed one or more signals, the controller further configured to generate and output to the display unit a query to a user as to whether to determine an insulin bolus dosage and, when a user selection to determine an insulin bolus dosage is detected, entering a bolus dosage determination mode, and when a user selection to not determine an insulin bolus dosage is detected, storing the processed one or more signals;
wherein when the bolus dosage determination mode is entered, the controller unit is further configured to output to the display unit a list of programmed bolus dosage determination options, and in response to a user selection of one of the programmed bolus dosage determination options from the list of programmed bolus dosage determination options, executing the selected one of the programmed bolus dosage determination options; and
wherein when the test strip is received within a predetermined time period of a meal event, a carbohydrate bolus determination mode is automatically selected.

2. The apparatus of claim 1, wherein the controller unit is further configured to display on the display unit the bolus dosage determined based on the execution of the selected one of the programmed bolus dosage determination options.

3. The apparatus of claim 2 wherein the displayed bolus dosage is one or more of an alphanumeric display, a graphical display, a video display, an audio display, a vibratory output, or combinations thereof.

4. The apparatus of claim 1 further including an output unit configured to provide one or more of an audible notification, a vibratory notification, or combinations thereof.

5. The apparatus of claim 1 wherein the list of programmed bolus dosage determination options includes one or more of a carbohydrate bolus, a correction bolus, an extended bolus, a dual bolus, or combinations thereof.

6. The apparatus of claim 1 further including an input unit coupled to the housing to receive the user selection to determine the insulin bolus dosage or the user selection to not determine the insulin bolus dosage.

7. The apparatus of claim 6 wherein the input unit includes one or more of an input button, a touch sensitive screen, a jog wheel, or combinations thereof.

8. The apparatus of claim 1 wherein the data received from the test strip corresponds to an analyte level.

9. The apparatus of claim 8 wherein the analyte level includes a glucose level of a patient.

10. The apparatus of claim 1 wherein the predetermined time period is within one hour prior to a meal event.

11. The apparatus of claim 1 wherein the data storage unit stores the user's insulin sensitivity information, and wherein the bolus dosage is determined based at least in part on the user's insulin sensitivity information.

12. The apparatus of claim 1 wherein the apparatus is configured to alert the user if a predetermined bolus time period has not passed since a previous bolus administration.

13. A computer program product for use with a glucose meter, the program product comprising a computer readable storage medium having a computer program stored thereon which controls the meter to process one or more signals associated with data received from a test strip, to store meal event information, to display a query to a user as to whether to calculate an insulin bolus dosage and, when a user selection to determine an insulin bolus dosage is detected, to instruct the meter to enter a bolus dosage determination mode, and when a user selection to not determine an insulin bolus dosage is detected, to instruct the meter to store the processed one or more signals, wherein when the bolus dosage determination mode is entered, the computer program further controls the meter to output a list of programmed bolus dosage determination options, and in response to a user selection of one of the programmed bolus dosage determination options from the list of programmed bolus dosage determination options, to execute the selected one of the programmed bolus dosage determination options, wherein when the test strip is received within a predetermined time period of a meal event, the computer program instructs the glucose meter to automatically select a carbohydrate bolus determination mode.

14. The computer program product of claim 13 wherein the computer program instructs the glucose meter to display the bolus dosage determined based on the execution of the selected one of the programmed bolus dosage determination options.

15. The computer program product 14 wherein the bolus dosage displayed on the glucose meter is one or more of an alphanumeric display, a graphical display, a video display, an audio display, a vibratory output, or combinations thereof.

16. The computer program product of claim 13 wherein the list of programmed bolus dosage determination options includes one or more of a carbohydrate bolus, a correction bolus, an extended bolus, a dual bolus, or combinations thereof.

17. A method, comprising:
storing meal event information;
receiving an analyte sample;
determining an analyte level corresponding to the analyte sample;
displaying the determined analyte level on a display unit;
generating and outputting on the display unit a query to a user as to whether to determine a bolus dosage; and
when a user selection to determine a bolus dosage is detected, entering a bolus dosage determination mode, and when a user selection to not determine a bolus dosage is detected, storing the analyte level, wherein when the bolus dosage determination mode is entered, outputting to the display unit a list of programmed bolus dosage determination options, and in response to a user selection of one of the programmed bolus dosage determination options from the list of programmed bolus dosage determination options, executing the selected one of the programmed bolus dosage determination options, and when the analyte sample is received within a predetermined time period of a meal event, automatically selecting a carbohydrate bolus determination mode.

18. The method of claim 17 further including displaying the bolus dosage determined based on the execution of the selected one of the programmed bolus dosage determination options.

19. The method of claim 17 further including generating one or more of an audible notification, a vibratory notification, a visual notification, or combinations thereof, associated with one or more of the determined bolus dosage based on the execution of the selected one of the programmed bolus dosage determination options, the determined analyte level, or combinations thereof.

20. The method of claim 17 wherein the list of programmed bolus dosage determination options includes one or more of a carbohydrate bolus, a correction bolus, an extended bolus, a dual bolus, or combinations thereof.

21. The method of claim 17 wherein the analyte level includes a measured glucose level of a patient and the bolus dosage is an insulin bolus dosage.

22. The method of claim 17 wherein outputting on the display unit the query to the user comprises displaying a prompt on the display unit.

23. The method of claim 22 further comprising prompting a user to provide an estimate of a carbohydrate amount to be ingested.

24. The method of claim 22 further comprising prompting a user to provide a time duration information for the determined bolus dosage.

25. The method of claim 17 wherein determining the bolus dosage is further based on a time difference between the determining the glucose level and a predetermined time period of a meal event.

26. The method of claim 17 wherein the analyte level is a glucose level and the bolus dosage is an insulin bolus dosage.

* * * * *